United States Patent
Parvizi et al.

(10) Patent No.: US 12,324,670 B2
(45) Date of Patent: Jun. 10, 2025

(54) METHODS AND APPARATUS FOR ELECTRODE PLACEMENT AND TRACKING

(71) Applicant: Ceribell, Inc., Sunnyvale, CA (US)

(72) Inventors: Josef Parvizi, Palo Alto, CA (US); Xingjuan Chao, Palo Alto, CA (US); Bradley G. Bachelder, Menlo Park, CA (US); Raymond Woo, Los Altos, CA (US); Mathew A. Herron, Hayward, CA (US); Vahid Saadat, Atherton, CA (US); Alexander M. Grant, Redwood City, CA (US); Jianchun Yi, San Jose, CA (US)

(73) Assignee: Ceribell, Inc., Sunnyvale, CA (US)

( * ) Notice: Subject to any disclaimer, the term of this patent is extended or adjusted under 35 U.S.C. 154(b) by 32 days.

(21) Appl. No.: 17/564,131

(22) Filed: Dec. 28, 2021

(65) Prior Publication Data

US 2022/0117535 A1    Apr. 21, 2022

Related U.S. Application Data

(63) Continuation of application No. 17/089,586, filed on Nov. 4, 2020, now Pat. No. 12,150,769, which is a
(Continued)

(51) Int. Cl.
*A61B 5/291*   (2021.01)
*A61B 5/00*    (2006.01)
(Continued)

(52) U.S. Cl.
CPC ............... *A61B 5/291* (2021.01); *A61B 5/324* (2021.01); *A61B 5/325* (2021.01); *A61B 5/6803* (2013.01);
(Continued)

(58) Field of Classification Search
CPC ......... A61B 5/291; A61B 5/325; A61B 5/324; A61B 5/6803; A61B 5/721; A61B 2562/043; A61B 2562/14; A61B 2562/164
See application file for complete search history.

(56) References Cited

U.S. PATENT DOCUMENTS

| 3,474,775 A | 10/1969 | William |
| 3,580,240 A | 5/1971 | Cosentino |

(Continued)

FOREIGN PATENT DOCUMENTS

| CN | 103124583 A | 5/2013 |
| CN | 103961090 A | 8/2014 |

(Continued)

OTHER PUBLICATIONS

Advanced Brain Monitoring (2022). B-Alert® X Series Mobile EEG, Located at www.advancedbrainmonitoring.com/products/b-alert-x-series, 5 pages.
(Continued)

*Primary Examiner* — Adam Z Minchella
(74) *Attorney, Agent, or Firm* — Cooley LLP

(57) ABSTRACT

An electrode carrier system includes one or more electrode assemblies having an electrode body. One or more tubular members extend from the electrode body and define a lumen terminating in a distal opening. The electrode assemblies carry a reservoir containing a conductive fluid or gel. The reservoir is in fluid communication with the lumens in the tubular members, and the electrode assemblies are typically supported on a backing which may optionally be configured as a headband. Systems are for tracking patient movement may be used in combination with the electrode carrier system.

30 Claims, 17 Drawing Sheets

Related U.S. Application Data continuation of application No. 15/783,346, filed on Oct. 13, 2017, now Pat. No. 10,888,240, which is a continuation of application No. 15/387,381, filed on Dec. 21, 2016, now Pat. No. 9,820,670.

(60) Provisional application No. 62/314,873, filed on Mar. 29, 2016.

(51) Int. Cl.
  *A61B 5/324* (2021.01)
  *A61B 5/325* (2021.01)

(52) U.S. Cl.
  CPC ........ *A61B 5/721* (2013.01); *A61B 2562/043* (2013.01); *A61B 2562/14* (2013.01); *A61B 2562/164* (2013.01)

(56) References Cited

U.S. PATENT DOCUMENTS

| | | |
|---|---|---|
| 3,602,216 A | 8/1971 | Lucas |
| 3,776,228 A | 12/1973 | Semler |
| 3,830,227 A | 8/1974 | Green |
| 3,830,229 A | 8/1974 | Johnson |
| 3,896,790 A | 7/1975 | Dikmen |
| 4,033,334 A | 7/1977 | Fletcher et al. |
| 4,079,731 A | 3/1978 | Danby |
| 4,137,909 A | 2/1979 | Hix |
| 4,166,457 A * | 9/1979 | Jacobsen .............. A61B 5/324 600/397 |
| 4,215,696 A | 8/1980 | Bremer et al. |
| 4,458,687 A | 7/1984 | Dickson |
| 4,537,198 A | 8/1985 | Corbett |
| 4,692,711 A | 9/1987 | Miyasako |
| 4,693,711 A | 9/1987 | Bremer et al. |
| 4,709,702 A | 12/1987 | Sherwin |
| 4,800,888 A | 1/1989 | Itil et al. |
| 4,919,148 A | 4/1990 | Muccio |
| 5,037,380 A | 8/1991 | Jacobsen et al. |
| 5,038,782 A | 8/1991 | Gevins et al. |
| 5,273,037 A | 12/1993 | Itil et al. |
| 5,309,909 A | 5/1994 | Gadsby et al. |
| 5,357,957 A | 10/1994 | Itil et al. |
| 5,404,875 A | 4/1995 | Gevins et al. |
| 5,628,729 A | 5/1997 | Okabe |
| 5,724,984 A | 3/1998 | Arnold et al. |
| 6,032,064 A | 2/2000 | Devlin et al. |
| 6,161,030 A | 12/2000 | Levendowski et al. |
| 6,201,982 B1 * | 3/2001 | Menkes .............. A61B 5/411 600/386 |
| 6,366,795 B1 | 4/2002 | Bremer et al. |
| 6,381,481 B1 | 4/2002 | Levendowski et al. |
| 6,510,333 B1 | 1/2003 | Licata et al. |
| 6,526,303 B1 | 2/2003 | Scampini |
| 6,640,118 B2 | 10/2003 | Van Heerden et al. |
| 6,640,122 B2 | 10/2003 | Manoli et al. |
| 6,654,626 B2 | 11/2003 | Devlin et al. |
| 6,952,605 B1 | 10/2005 | Scarberry |
| 7,424,319 B2 | 9/2008 | Muehlsteff et al. |
| 7,841,301 B2 | 11/2010 | Mainini et al. |
| 8,103,328 B2 | 1/2012 | Turner et al. |
| 8,201,330 B1 * | 6/2012 | Rood .............. A61B 5/25 29/882 |
| 8,428,682 B1 | 4/2013 | Rood et al. |
| 8,568,416 B2 | 10/2013 | Schmitz et al. |
| 8,594,763 B1 | 11/2013 | Bibian et al. |
| 8,700,122 B2 | 4/2014 | Cordero et al. |
| 8,805,470 B2 | 8/2014 | Afanasewicz et al. |
| 9,173,670 B2 | 11/2015 | Sepulveda et al. |
| 9,345,418 B2 | 5/2016 | Alkire |
| 9,408,575 B2 | 8/2016 | Bordoley et al. |
| 9,439,599 B2 | 9/2016 | Thompson et al. |
| 9,820,670 B2 | 11/2017 | Parvizi et al. |
| 10,433,756 B1 | 10/2019 | Bachelder et al. |
| 10,888,240 B2 | 1/2021 | Parvizi et al. |
| 11,357,434 B2 | 6/2022 | Bachelder et al. |
| 12,150,769 B2 | 11/2024 | Parvizi et al. |
| 2001/0044573 A1 | 11/2001 | Manoli et al. |
| 2002/0029005 A1 * | 3/2002 | Levendowski ...... A61B 5/6804 600/545 |
| 2002/0173710 A1 | 11/2002 | Licata |
| 2007/0004978 A1 | 1/2007 | Ponton |
| 2007/0010729 A1 | 1/2007 | Virtanen et al. |
| 2007/0027448 A1 | 2/2007 | Paul et al. |
| 2007/0255127 A1 | 11/2007 | Mintz et al. |
| 2007/0270678 A1 | 11/2007 | Fadem et al. |
| 2007/0272313 A1 | 11/2007 | Olds |
| 2008/0027345 A1 | 1/2008 | Kumada et al. |
| 2008/0154112 A1 | 6/2008 | Murphy et al. |
| 2008/0215128 A1 | 9/2008 | Rainey et al. |
| 2009/0107417 A1 | 4/2009 | Mainini et al. |
| 2010/0030299 A1 | 2/2010 | Covalin |
| 2011/0054288 A1 | 3/2011 | Besio |
| 2012/0143020 A1 * | 6/2012 | Bordoley .............. A61B 5/291 600/383 |
| 2012/0190959 A1 | 7/2012 | Hayakawa et al. |
| 2015/0065838 A1 | 3/2015 | Wingeier et al. |
| 2015/0112153 A1 | 4/2015 | Nahum |
| 2015/0313498 A1 | 11/2015 | Coleman et al. |
| 2016/0022165 A1 | 1/2016 | Sackellares et al. |
| 2016/0022981 A1 | 1/2016 | Wingeier et al. |
| 2016/0324473 A1 | 11/2016 | Mortara et al. |
| 2017/0143228 A1 | 5/2017 | Leuthardt, Jr. et al. |
| 2017/0165485 A1 | 6/2017 | Sullivan et al. |
| 2017/0281036 A1 | 10/2017 | Parvizi et al. |
| 2018/0049661 A1 | 2/2018 | Parvizi et al. |
| 2018/0289945 A1 | 10/2018 | Lampo |
| 2019/0021664 A1 | 1/2019 | Kesinger et al. |
| 2019/0192030 A1 | 6/2019 | Watson et al. |
| 2019/0192078 A1 | 6/2019 | Sargent et al. |
| 2019/0365270 A1 | 12/2019 | Bradley et al. |
| 2021/0128044 A1 | 5/2021 | Parvizi et al. |
| 2022/0117536 A1 | 4/2022 | Parvizi et al. |
| 2023/0000416 A1 | 1/2023 | Bachelder et al. |

FOREIGN PATENT DOCUMENTS

| | | |
|---|---|---|
| CN | 104068852 A | 10/2014 |
| CN | 104068853 A | 10/2014 |
| CN | 105324075 A | 2/2016 |
| CN | 107073260 A | 8/2017 |
| DE | 2644236 A1 | 4/1978 |
| JP | S-57160438 A | 10/1982 |
| JP | 03-085005 U | 8/1991 |
| JP | 2008-544775 A | 12/2008 |
| JP | 2010-051356 A | 3/2010 |
| JP | 2012-110535 A | 6/2012 |
| JP | 2016-530897 A | 10/2016 |
| WO | WO-01/01856 A1 | 1/2001 |
| WO | WO-2014/152806 A1 | 9/2014 |
| WO | WO-2015/044851 | 4/2015 |
| WO | WO-2015/055156 A1 | 4/2015 |
| WO | WO-2015/196554 A1 | 12/2015 |
| WO | WO-2017/172742 A1 | 10/2017 |
| WO | WO-2019/231897 A1 | 12/2019 |

OTHER PUBLICATIONS

Corrected Notice of Allowability mailed on Aug. 31, 2017, for U.S. Appl. No. 15/387,381, filed Dec. 21, 2016, 2 pages.
Corrected Notice of Allowability mailed on Sep. 9, 2019, for U.S. Appl. No. 16/017,568, filed Jun. 25, 2018, 2 pages.
Extended European Search Report mailed on Jan. 24, 2022, for EP Application No. 19 810 869.8, filed on May 28, 2019, 7 pages.
Extended European Search Report mailed on Oct. 11, 2019, for EP Application No. 17 776 445.3, filed on Mar. 28, 2017, 8 pages.
Final Office Action mailed on Jul. 15, 2020, for U.S. Appl. No. 15/783,346, filed Oct. 13, 2017, 9 pages.
Final Office Action mailed on May 19, 2021, for U.S. Appl. No. 16/410,297, filed May 13, 2019, 18 pages.

(56) References Cited

OTHER PUBLICATIONS

Final Office Action mailed on Aug. 7, 2023, for U.S. Appl. No. 17/836,969, filed Jun. 9, 2022, 29 pages.
International Search Report and Written Opinion mailed on Aug. 1, 2019, for PCT Application No. PCT/US2019/034149, filed on May 28, 2019, 8 pages.
International Search Report and Written Opinion mailed on Jul. 31, 2017, for PCT Application No. PCT/US2017/024505, filed on Mar. 28, 2017, 11 pages.
Non-Final Office Action mailed on Apr. 18, 2017, for U.S. Appl. No. 15/387,381, filed Dec. 21, 2016, 8 pages.
Non-Final Office Action mailed on Jan. 11, 2019, for U.S. Appl. No. 16/017,568, filed Jun. 25, 2018, 8 pages.
Non-Final Office Action mailed on Apr. 7, 2020, for U.S. Appl. No. 15/783,346, filed Oct. 13, 2017, 8 pages.
Non-Final Office Action mailed on Mar. 3, 2021, for U.S. Appl. No. 16/410,297, filed May 13, 2019, 16 pages.
Non-Final Office Action mailed on Jan. 20, 2023, for U.S. Appl. No. 17/836,969, filed Jun. 9, 2022, 30 pages.
Non-Final Office Action mailed on Aug. 24, 2023, for U.S. Appl. No. 17/089,586, filed Nov. 4, 2020, 10 pages.
Non-Final Office Action mailed on Sep. 8, 2023, for U.S. Appl. No. 17/564,135, filed on Dec. 28, 2021, 14 pages.
Notice of Allowance mailed on Feb. 15, 2022, for U.S. Appl. No. 16/410,297, filed May 13, 2019, 10 pages.
Notice of Allowance mailed on Jul. 24, 2017, for U.S. Appl. No. 15/387,381, filed Dec. 21, 2016, 9 pages.
Notice of Allowance mailed on Aug. 3, 2018, for U.S. Appl. No. 13/905,377, filed May 30, 2013, 5 pages.
Notice of Allowance mailed on May 6, 2019, for U.S. Appl. No. 16/017,568, filed Jun. 25, 2018, 5 pages.
Notice of Allowance mailed on Aug. 5, 2020, for U.S. Appl. No. 15/783,346, filed Oct. 13, 2017, 10 pages.
Extended European Search Report mailed on Jul. 26, 2023, for EP Application No. 23 170 663.1. filed on Mar. 28, 2017, 8 pages.
Final Office Action mailed on Feb. 2, 2024, for U.S. Appl. No. 17/564,135, filed on Dec. 28, 2021, 16 pages.
Final Office Action mailed on Mar. 29, 2024, for U.S. Appl. No. 17/089,586, filed Nov. 4, 2020, 11 pages.
Non-Final Office Action mailed on Feb. 21, 2024, for U.S. Appl. No. 17/836,969, filed Jun. 9, 2022, 32 pages.
Corrected Notice of Allowability mailed on Aug. 8, 2024, for U.S. Appl. No. 17/089,586, filed Nov. 4, 2020, 2 pages.
Final Office Action mailed on Sep. 5, 2024, for U.S. Appl. No. 17/836,969, filed Jun. 9, 2022, 16 pages.
Non-Final Office Action mailed on Jun. 21, 2024, for U.S. Appl. No. 17/564,135, filed on Dec. 28, 2021, 17 pages.
Notice of Allowance mailed on Jul. 19, 2024, for U.S. Appl. No. 17/089,586, filed Nov. 4, 2020, 9 pages.
Final Office Action mailed on Oct. 10, 2024, for U.S. Appl. No. 17/564,135, filed on Dec. 28, 2021, 16 pages.
Li, G. et al. (2016). "Novel Passive Ceramic Based Semi-dry Electrodes for Recording Electroencephalography Signals from the Hairy Scalp," Sensors and Actuators B: Chemical 237:167-178.
Mota, A.R. et al. (2013). "Development of a quasi-dry electrode for EEG recording," Sensors and Actuators A 199:310-317.
Non-Final Office Action mailed on Mar. 14, 2025, for U.S. Appl. No. 17/836,969, filed Jun. 9, 2022, 17 pages.
Wang, F. et al. (2016). "Novel semi-dry electrodes for brain-computer interface applications," J. Neural. Eng. 13:046021, 15 pages.
Weder, M. et al. (2015). "Embroidered Electrode with Silver/Titanium Coating for Long-Term ECG Monitoring," Sensors 15:1750-1759.
Xing, X et al. (2018). "Assessing a novel micro-seepage electrode with flexible and elastic tips for wearable EEG acquisition," Sensors and Actuators A: Physical 270:262-270.

\* cited by examiner

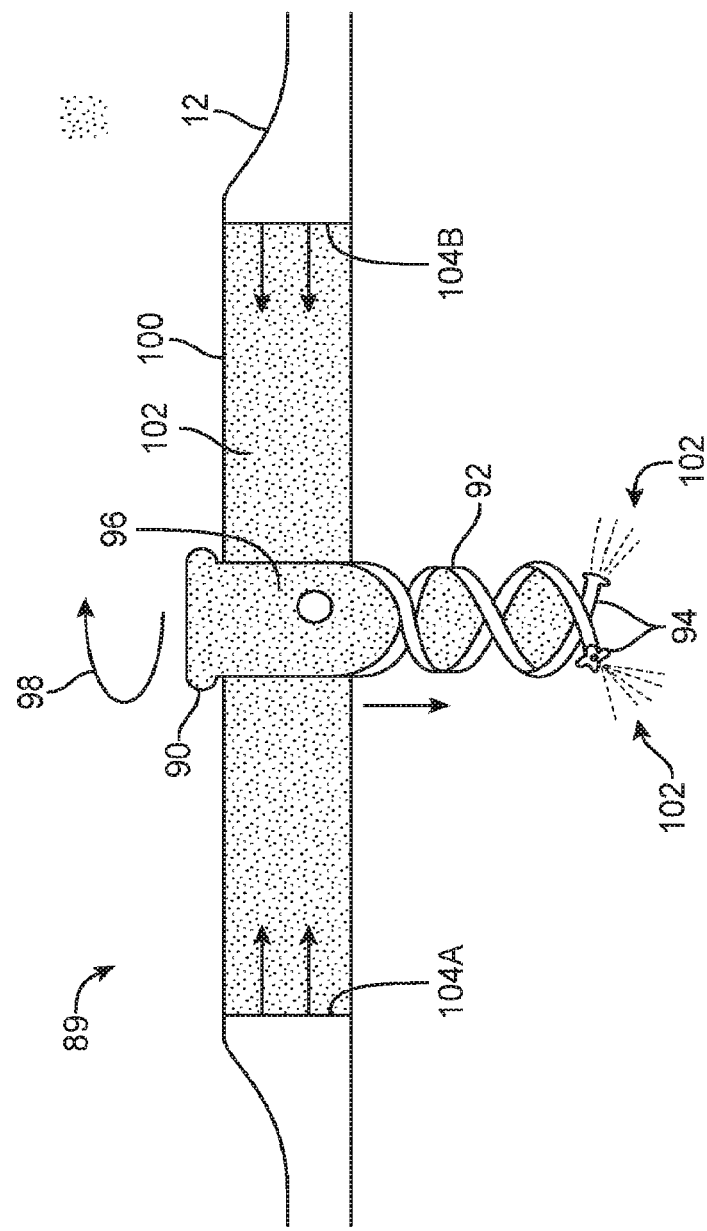

METHODS AND APPARATUS FOR ELECTRODE PLACEMENT AND TRACKING

CROSS-REFERENCE TO RELATED APPLICATIONS

This application is a continuation of U.S. patent application Ser. No. 17/089,586 filed on Nov. 4, 2020, which is a continuation of U.S. patent application Ser. No. 15/783,346 filed on Oct. 13, 2017, now U.S. Pat. No. 10,888,240, which is a continuation of U.S. patent application Ser. No. 15/387,381, filed Dec. 21, 2016, now U.S. Pat. No. 9,820,670, which claims the benefit of U.S. Provisional Application No. 62/314,873 filed on Mar. 29, 2016. Each of the foregoing disclosures is incorporated herein by reference in its entirety.

BACKGROUND OF THE INVENTION

1. Field of the Invention

The present invention relates to methods and apparatus for facilitating the placement of one or more electrodes against the skin surface of a patient and monitoring a patient status. More particularly, the present invention relates to methods and apparatus for facilitating the speed and efficiency for placing one or more electroencephalogram (EEG) electrodes against a patient's the scalp, optionally in combination with tracking the movements of a patient.

Electrodes typically used in electrocardiography and electroencephalography generally provide for uniform contact between the metal electrode and the skin to prevent electrical noise due to the interface between the electrode and skin surface. To provide for uniform contact with the skin area, a conductive gel may be applied to the skin surface to facilitate electrical conduction with the electrode. However, when electrodes are to be placed at multiple locations over the patient's scalp, the application of the gel in combination with determining electrode placement not only requires specialized training and skill but is also very time consuming.

Some electrodes utilize conductive gel interfaces which are pre-formed for contacting the electrode but the gel interfaces become ineffective when hair is present and may sometimes require the removal of the underlying hair.

It has been suggested the EEG electrodes may be formed with an on-board conductive gel dispenser for delivering the gel immediately after a placing a headgear on a patient. See, U.S. Pat. No. 6,640,122. The devices of the '122 patent, however, do not provide for preserving the gel as a component of the electrode for extended time periods.

Accordingly, there exists a need for methods and devices which facilitate the speed of placing electrodes and also for facilitating contact between the electrode and the skin surface even in the presence of hair without requiring manually prepare the hair and scalp for each electrode contact. It would be particularly desirable if such methods and devices could provide for incorporation of a conductive fluid or gel as part of the electrode assembly as well as for preserving such conductive fluids or gels for extended time periods. At least some of these needs will be met by the inventions described and claimed herein.

2. Description of the Background Art

EEG electrodes having plungers and/or capsules for dispensing conductive gels are described in U.S. Pat. Nos. 9,408,575; 8,805,470; 6,640,122 and U.S. Patent Publication No. 2007/0255127. U.S. Pat. No. 6,381,481 describes an EEG electrode with fingers for spreading hair. Other patents of interest include U.S. Pat. Nos. 7,841,301; 4,709,702; 5,273,037; and 5,357,957; 4,166,457; 4,079,731; 4,033,334; 3,830,229; and U.S. Patent Publication No. 2007/0272313. Headgear including integrated EEG electrodes are available commercially from Advanced Brain monitoring, Inc., Carlsbad, California, under the tradename B-Alert® Mobile EEG (http://www.advancedbrainmonitoring.com) and from Hydrodot, Inc., Westford, Massachusetts, under the tradename StatNet™ EEG headpiece (http://www.hydrodot.net).

SUMMARY OF THE INVENTION

Generally, in facilitating the placement and contact of electrodes upon the selected areas of the skin surface, an electrode carrier system may generally comprise an electrode body which is at least partially electrically conductive, one or more tubular members extending from the electrode body, each of the one or more tubular members defining a lumen therethrough and a distal opening, a reservoir having a compressible structure and containing a conductive fluid or gel which is in fluid communication with the one or more tubular members, and a backing supporting the electrode body and reservoir.

In other variations, the electrode carrier system may generally comprise an electrode body having one or more tubular members extending therefrom, each of the tubular members defining a lumen therethrough and a distal opening, a reservoir having a compressible structure which defines an internal volume and which is in fluid communication with the one or more tubular members, and a controller and/or output device which is in electrical communication with the electrode body, wherein the controller and/or output device is configured to receive electrical signals from the electrode assembly and record and/or output a corresponding response.

The electrode carrier system may generally comprise a backing secured around the head of a patient. The backing may be configured as a headband although the carrier system may be incorporated into any number of other platforms or positioning mechanisms for maintaining the electrodes against the patient body. The individual electrodes are spaced apart from one another so that when the headband is positioned upon the patient's head, the electrodes are aligned optimally upon the head for receiving EEG signals. The carrier system may have each of the electrodes electrically coupled via corresponding conductive wires extending from the backing and coupled, e.g., to a controller and/or output device. Although in other variations, the electrodes may be coupled to the controller and/or output device wirelessly.

The controller and/or output device may generally comprise any number of devices for receiving the electrical signals such as electrophysiological monitoring devices and may also be used in combination with any number of brain imaging devices, e.g., fMRI, PET, NIRS, etc.

The electrodes, as described herein, may be positioned upon the backing to quickly enable conductive contact with the underlying skin while allowing for patient comfort such as when the patient is reclined with the back or side of their head resting upon a surface without discomfort from the electrodes.

In one variation of the electrode carrier system, each of the electrodes may be configured to include a visual or haptic indicator to provide feedback to the user that sufficient electrode connection with the skin surface has been achieved. For instance, each electrode may incorporate an impedance sensor and indicator such that when the controller and/or output device detects a relatively low impedance, e.g., 5-50 kΩ, in a particular electrode, that electrode may have its indicator (such as an LED) actuated to indicate that sufficient electrical contact between the electrode and underlying skin is achieved.

Turning now to the electrode configurations, one variation of an electrode carrier system may comprise each of the electrodes enclosed within a reservoir which is pre-filled with a conductive gel or fluid. Each electrode may be configured into a flattened or atraumatic configuration which is contained within a respective reservoir and each reservoir may be formed of any number of flexible materials, e.g., silicone, polyurethane, rubber, etc., which can readily collapse. The electrodes may be coupled via conductive wires passing through a lumen defined through the backing separated from the electrodes by a substrate. Each reservoir may also respectively define one or more openings through which the conductive gel or fluid may be expelled.

Once the platform has been situated over the patients' head, the user may press upon each of the reservoirs such that the conductive fluid or gel flows through the openings and onto the skin of the patient. The conductive fluid or gel expelled through the openings may maintain fluid communication between the skin surface and the respective electrodes such that the detected electrical signals may be transmitted from the skin and to the electrodes. Moreover, because of the flexibility of the reservoirs, once the conductive fluid or gel has been expelled into contact with the skin surface, the backing may lie flat against the skin surface so that the patient may comfortably lay their head upon a surface while still maintaining electrical contact with the electrodes.

Another electrode variation may be comprised of one or more loops of conductive wire or ribbon which are able to readily bend or flex against the skin surface. The electrode carrier system may include a pressure release reservoir for containing the conductive fluid or gel, as described above, around each of the electrodes so that the conductive fluid or gel may be expelled around and within the one or more loops to ensure a conductive path.

Another variation may be configured into one or more tubular members which extend from the backing transversely. The tubular members may be each arranged in a circular pattern for each electrode and they may also define a lumen therethrough with an opening defined at each distal end. Each of the tubular members may be fabricated from a conductive metal which may retain its tubular shape when in use or which may be sufficiently thin and flexible to bend or yield when placed against the patient's skin surface. Alternatively, the tubular members may be fabricated from a flexible material which is coated or layered with a conductive material such that the members retain their flexibility. In either case, the conductive fluid or gel may be either contained within the tubular members or they may be retained within a pressure release reservoir, as described above, surrounding or in proximity to each electrode. Because the tubular shape of the electrodes, they may readily pass through the patient's hair, if present, and into contact against the skin surface while maintaining electrical contact.

Yet another variation of an electrode embodiment may also utilize a pressure release reservoir filled with the conductive fluid or gel. The reservoir may be formed of a flexible material, e.g., silicone, polyurethane, rubber, etc., extending from the backing to form a curved or arcuate structure with one or more openings defined over the reservoir. These openings may remain in a closed state until a force is applied to the reservoir and/or backing which may urge the fluid or gel contained within to escape through the openings and into contact with the outer surface of the reservoir and underlying skin surface. The outer surface of the reservoir may have a layer of conductive material in electrical contact with the conductive wires so that once the fluid or gel has been expelled from within the reservoir and out onto the conductive material upon the reservoir outer surface and skin surface, electrical contact may be achieved.

In yet another variation, an electrode carrier system having an electrode body may define one or more tubular members extending from the body such that the members project transversely away from the backing. The electrode body may be comprised of a conductive material such as a metal which may be rigid. However, in other variations, the body may be fabricated from a conductive material which is also flexible, e.g., conductive silicone, and/or from a flexible material, e.g., silicone, polyurethane, rubber, etc., which may be coated or layered with a conductive material such that the underlying tubular members retain their flexibility.

In either case, the body may be secured to the backing such that the one or more openings are defined along the body and extending through the members are in fluid communication with a reservoir having a compressible housing. The reservoir may also be secured to the backing and contain a volume of conductive fluid or gel local to the electrode body. The tubular members may be arranged in a uniform pattern or in an arbitrary pattern as well and while the members are shown arranged in a circular configuration, other patterns may be implemented. When the backing has been secured to the patient, the reservoir may be pressed or urged such that the fluid or gel contained within is expelled through each of the tubular members and into contact against the underlying skin surface through corresponding distal openings. The elongate nature of the members may enable them to pass readily through the patient's hair, if present, and into direct contact against the skin surface.

In another variation, an electrode carrier system having a tubular body may define one or more openings over its surface. The tubular body may have one or more tubular members which extend in a spiral or helical pattern away from the backing. The tubular members may define a lumen therethrough which extends from the tubular body and to a distal opening at its tip. The backing may further define a reservoir which contains a volume of conductive fluid or gel such that the body is in fluid communication with the reservoir. Additionally and/or alternatively, the distal tips of the members may present a roughened surface for contacting the skin. The optionally roughened tips may be rotated or otherwise translated or moved across over the skin surface by the user to at least partially exfoliate the skin surface to facilitate electrical contact.

In particular, a distal skin-contacting surface of the electrode assembly may be modified to prepare the skin surface to enhance electrical conductance (.i.e. lower electrical resistance) between an electrically conductive portion of the electrode assembly and the skin when that electrically conductive portion is in physical contact with the skin. For example, the tissue-contacting surface(s) of the electrode assembly may be modified to have an abrasive surface, e.g. by coating with abrasive particulate; may be formed or molded to have protruding rigid features, e.g. bumps, ridges, or the like; and/or may be coated with a material that lowers the electrode connection impedance. Such sweeping and/or chemical coating of the tissue-contacting surface(s) of the electrode assembly over the target tissue location could scrub, dissolve and/or otherwise disrupt dead tissue and break-up scalp oil. In specific examples, at least a portions of a distal tissue-contacting surface of the electrode assembly, for example the distal surface(s) of at least some of the tubular members, comprise such surface features, surface coatings, surface treatments, or combination thereof to improve the quality of the electrode connection.

In yet another variation, the electrode carrier system may also be utilized for other applications such as patient motion tracking employing either visual motion tracking or accelerometers. The motion tracking may be coupled with an EEG device to reject EEG data during heavy movements. The visual motion tracking allows the camera to automatically track the patient with the headband and offers recording precision as well as more mobility to patients.

In another specific aspect of the present invention, an electrode assembly comprises an electrode body and one or more tubular members extending from the electrode body, typically from a bottom surface of the electrode body. Each tubular member has a distal tip, and at least some of the tubular members have a lumen with a distal opening in the distal tip. A reservoir containing a conductive fluid or gel is optionally disposed in the electrode body, and the electrode body is configured for dispensing the conductive fluid or gel from the reservoir through the lumen(s) and out of the distal opening(s) of the tubular member(s). Alternatively, in some embodiments, the conductive fluid or gel may be dispended onto or through the lumens of the tubular member using a syringe or other separate delivery device.

As used herein, the term "conductive" will mean electrically conductive, i.e. having a very low electrical resistance and the ability to carry low current biological signals such as EEG signals.

As further used herein, the phrase "tubular member" will mean a generally elongated structure, i.e. having a length extending away from the bottom of the electrode body greater than its width parallel to the bottom of the electrode body, where the width is measured at its narrowest point. Usually, the length will be at least twice the width, frequently being at least three times the width. Exemplary tubular members may have generally circular horizontal peripheries (in a plane parallel to the bottom of the electrode body) making them generally cylindrical along a vertical axis. Other exemplary tubular members may have crescent-shaped horizontal peripheries.

In specific embodiments, the electrode assembly will typically comprise at least two tubular members, and may comprise three tubular members, four tubular members, or even more. The tubular members will usually depend vertically downwardly from a bottom surface of the electrode body and will be specifically configured so that they may penetrate a patient's hair so that a distal tip of the tubular members will be able to engage and provide reliable electrical contact with a patient's scalp. The tissue engagement areas of the tubular members on bottom surface of the electrode body will usually be 50% or less of the area of the bottom surface, frequently being 30% or less of the area of the electrode body, and usually being at least 5% of the area of the bottom surface. Thus, the tissue engagement areas of the tubular members on bottom surface of the electrode body will usually be in a range from 5% to 50% of the area of the bottom surface, typically being in a range from 5% to 30% of the area of the bottom surface.

In most instances, the tubular members will extend from a generally planar bottom of the electrode body at a perpendicular angle. In other instances, however, the tubular members may extend at an angle anywhere in the range from 30° to 150° relative to the plane, typically being from 60° to 120° relative to the plane. In other instances, however, the tubular members may have other configurations, for example being configured in a helical shape so that they may penetrate hair to a patient's scalp by rotating the electrode assembly around a vertical axis.

In other specific embodiments of the present invention, the distal tips of at least some of the tubular members will have a skin preparation, e.g. tissue-roughening, surface. For example, the tissue-roughening surface may comprise an abrasive material, such as a grit or other abrasive particles, formed over at least a portion of the distal tip of the tubular member. In other instances, the surface-roughening may comprise surface features, such as ridges, bumps, grooves, and the like, formed over at least a portion of the distal tip which contacts the patient's skin.

The electrode body, and in particular the tubular members connected to the electrode body, may be formed at least partly from electrically conductive materials, such as metals, electrically conductive coatings, embedded wires, or electrically conductive polymers. In such instances, the electrode body and/or the tubular members will provide at least a portion of the electrical path needed to conduct biological currents from the tip of the tubular member(s) to an electrical terminal or other conductive connector on the electrode body as described below. In other instances, however, the electrode body and/or the tubular members may be formed primarily or even entirely from an electrically non-conductive material. In such instances, the electrically conductive fluid or gel will provide most or all of the electrically conductive path needed to deliver the biological current from the distal tip of the tubular member to the electrical terminal after such conductive fluid or gel has been distributed throughout the electrode body and tubular member, as described in greater detail below.

The tubular members may comprise a variety of geometries. Often, the tubular members will be generally cylindrical having a lumen extending therethrough. In other instances, however, the tubular members may be formed as "prongs" having a relatively broad tissue-contacting region along a curved "axis" at their distal tips. In many instances, the tissue-contacting regions of the prongs will be generally crescent-shaped so that they will follow a generally circular path as they are rotated against the patient's tissue, as described in more detail below.

The prongs and other tubular members of the present invention will preferably have a port in their tissue-contacting surfaces for delivering the electrically conductive fluid or gel to the patient's skin. In some instances, ports may be formed in a generally flat bottom surface of the tubular members or prongs. In other instances, the ports may be connected to a channel or other distribution feature on the tissue-contacting surface of the prong or other tubular member. In still further specific embodiments, the ports for delivering the electrically conductive fluid or gel may be located in a recessed surface of the prong which may be adjacent to a tissue-contacting lower surface of the prong or other tubular member.

While the electrode assemblies will usually comprise one or more tubular members as just discussed, in some alternative embodiments, the electrode body may have a generally flat bottom free from tubular and other protruding members. The flat bottom will be configured to engage the skin and have openings to release a conductive fluid or gel in any of the ways described elsewhere herein for delivering the conductive fluid or gel through a tubular member. The tissue-contacting surface(s) of such flat bottoms may be modified in any of the ways discussed herein to have electrical conductivity with the target tissue surface(s).

The reservoir in the electrode body which contains the conductive fluid or gel will preferably be sealed to preserve the fluid or gel and allow the long-term storage of an electrode assembly which has been pre-filled with the electrically conductive fluid or gel. In specific embodiments, the reservoir will have a sealed dispensing container within the reservoir which may be incorporated into the electrode assembly during the initial manufacture thereof. For example, the sealed dispensing container may comprise a sealed dispensing container, e.g. a packet, which is constrained within a chamber in the electrode body, where the electrode body comprises a plunger configured to be manually pressed against the sealed dispensing container to deliver the electrically conductive fluid or gel from the sealed dispensing container through the lumen(s) and out of the distal opening(s) of the tubular member(s). In specific instances, the sealed dispensing container and the plunger will be located in an upper portion of the electrode body, and the tubular member(s) will extend from a lower surface of the electrode body. In such specific instances, the electrode body will be configured to define a flow path to deliver the conductive fluid or gel from the sealed dispensing container through the lumen(s) in the tubular member(s) and out of the distal opening(s) of the tubular member(s).

The electrode assemblies of the present invention may be provided with various mechanisms for releasing the electrically conductive fluid or gel from such a sealed dispensing container. For example, the reservoir may have a dispensing hole which is configured to define a rupture region on the sealed dispensing container when the sealed dispensing container is pressurized by the plunger. In other instances, however, the sealed dispensing container may comprise any one of a syringe, a manual squeeze tube, a roller squeeze tube, or the like, which are incorporated into or otherwise combined with the electrode body.

The electrode assemblies of the present invention will typically have an electrically conductive terminal mounted on the electrode body and configured to allow attachment of the electrode assembly to a controller or other instrumentation for measuring the EEG or other electrical biological signals. The electrically conductive terminal will be configured to electrical couple to wires or other conventional electrical conductors to provide a connection to the control system. In the disclosed embodiments, the electrically conductive terminal will have an interior portion which is located in and exposed to the flow path within the electrode body for the electrically conducted fluid or gel. In some instances, the electrically conductive terminal will be the only solid electrically conductive component which is part of the electrode assembly. The electrical conduction of the biological signal to the electrically conductive terminal may be provided entirely by the electrically conductive fluid or gel after such fluid or gen has been distributed throughout the electrode body. In other instances, however, additional electrically conductive components, coatings, wires, or the like, may be provided within the electrode body of the electrode assembly in order to provide or enhance electrical conductivity.

In further aspects of the present invention, an electrode carrier system comprises an elongated backing, typically figured as a headband or headgear for placement upon a patient's head. A plurality of electrode assemblies, as described above, are mounted on and distributed over a length of the elongated backing, and at least one electrically conductive wire or other conductor is connected to each of the electrode assemblies to deliver low current biological signals from the electrode assemblies to a separate controller and/or output device.

The systems of the present invention may further comprise the controller and/or output device configured to receive the low current biological signal from the electrode assemblies. Additionally, the controller may be configured to output a response corresponding to the electrical signals from the electrode assemblies. In preferred embodiments, the distal tips of at least some of the tubular members will define a tissue-roughening or other skin preparation surface and at least some of the electrode assemblies will be movably, e.g. rotatably, mounted on the elongated backing to allow a user to sweep or scrub the tissue-engaging surfaces of the assemblies over target tissue surface(s) to a abrade the tissue surface to enhance electrical contact. In particular, the electrode assemblies may be rotated or alternatively translated (pushed back-and-forth) over the contacting tissue surface after the elongated backing of the electrode carrier system has been mounted on the patient's head.

In a further specific aspect of the present invention, a plurality of electrodes may be placed on patient's scalp by placing a headband or other headgear around the patient's scalp. The headband carries a plurality of electrode assemblies, for example as described above, and distal tip(s) of one or more tubular members extending from at least some of the electrode assemblies are engaged against scalp tissue. An electrically conductive fluid or gel is then extruded from a reservoir disposed in at least some of the electrode assemblies so that the fluid or gel passes through the tubular members to form an electrically conductive path to the patient's scalp tissue. The plurality of electrode assemblies are connected to a controller and/or output device configured to receive low power biological current from the electrode assemblies. In the specific aspects of the methods of the present invention, the distal tips of at least some of the tubular members will be positioned through hair on the patient's scalp. At least some of the plurality of electrode assemblies may be rotated in order to abrade scalp tissue adjacent the distal tip(s) of said one or more tubular members in order to lower contact resistance between the electrode assembly and the scalp tissue. Usually, at least some of the tubular members define the skin preparation, e.g. tissue-roughening surface, and the electrically conductive fluid or gel is extruded from the reservoir through the lumens into the tubular members and out the distal opening(s) on the distal tips of the tubular member(s) onto the scalp tissue. In specific instances, the electrically conductive fluid or gel may be extruded out of or through grooves on the distal tips of the tubular members. Such extrusion typically comprises manually applying external pressure to a sealed dispensing container which holds the electrically conductive fluid or gel, or the sealed dispensing container is incorporated into the electrode assembly, typically being disposed in a chamber within a electrode body. In specific instances, applying external pressure to the sealed dispending containers may comprise pressing a plunger to engage a rupturable sealed dispensing container that carries the electrically conductive fluid or gel. Alternatively, applying external pressure to the sealed dispensing container may comprise manually squeezing a tube, manually depressing a syringe plunger, rolling a squeezed tube, or the like. In many instances, the electrically conductive path to the patient's scalp tissue is formed solely by the conductive fluid or gel. In other instances, however, the electrically conducted path to the patient's scalp may be formed at least party by an electrically conductive structure on the tubular member or elsewhere within the electrode assembly.

BRIEF DESCRIPTION OF THE DRAWINGS

FIG. 8 illustrates a partial cross-sectional side view of another variation where each electrode is configured into a helical configuration which may be rotated relative to the supporting platform.

DETAILED DESCRIPTION OF THE INVENTION

Figure 1:
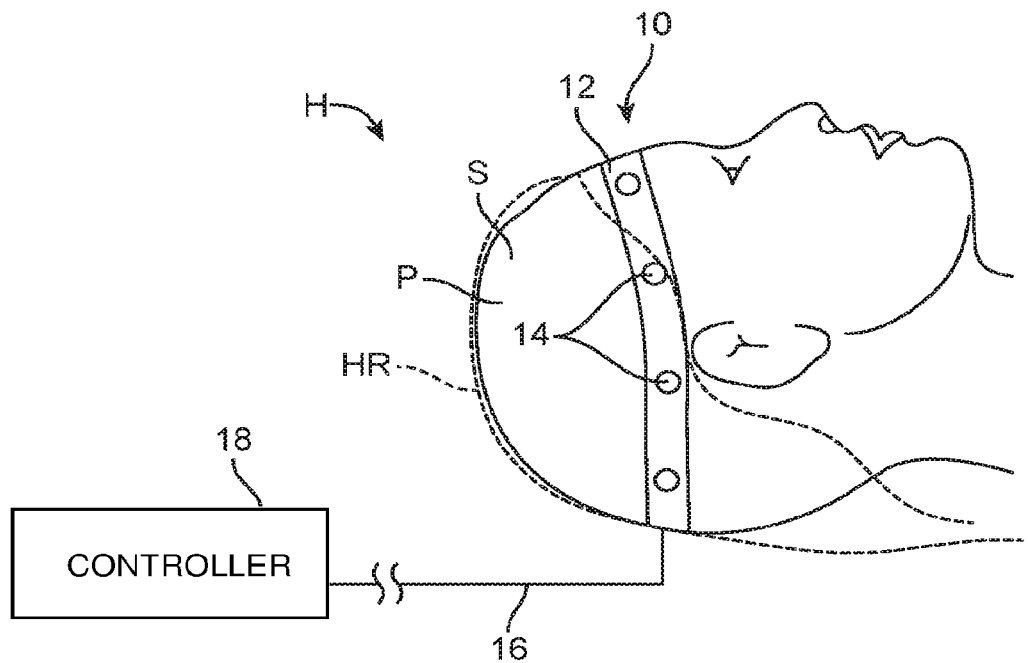
FIG. 1 illustrates a side view of a patient with an electrode carrier system configured as a headband.

The electrode carrier system 10 may generally comprise a backing 12 shown in the side view of FIG. 1 which illustrates the carrier system 10 secured around the head H of patient P. The backing 12 is shown configured as a headband in this variation although the carrier system 10 may be incorporated into any number of other platforms or positioning mechanisms for maintaining the electrodes against the patient body. The backing 12 is shown configured as a headband in this variation and the individual electrode assemblies 14 are spaced apart from one another so that when the headband is positioned upon the patient's head H, the electrode assemblies 14 are aligned optimally upon the head H for receiving EEG signals. The electrode carrier system 10 may have each of the electrodes assemblies 14 electrically coupled via corresponding conductive wires 16 extending from the backing 12 and coupled, e.g., to a controller and/or output device 18. Although in other variations, the electrodes assemblies 14 may be coupled to the controller and/or output device 18 wirelessly.

The controller and/or output device 18 may generally comprise any number of devices for receiving the electrical signals such as electrophysiological monitoring devices and may also be used in combination with any number of brain imaging devices, e.g., fMRI, PET, NIRS, etc. In one particular variation, the electrode embodiments described herein may be used in combination with devices such as those which are configured to receive electrical signals from the electrodes and process them.

The electrodes assemblies A4, as described herein, may be positioned upon the backing 12 to quickly enable conductive contact with the underlying skin while allowing for patient comfort such as when the patient P is reclined, as shown, with the back or side of their head H resting upon a surface without discomfort from the electrodes 14.

One challenge in ensuring that the individual electrodes 14 make sufficient contact with the underlying skin is the presence of hair HR on the scalp S of the patient P. Prior to the present invention, the region where the electrodes assemblies 14 are placed upon the scalp S were typically shaved to remove excess hair (if present) which interferes and inhibits electrical contact between the electrode assemblies 14 and the scalp surface. In contrast, the electrode carrier assemblies of the present invention as described herein enable rapid reliable electrical contact on individual electrode assemblies through the hair HR and with scalp surface without having to remove the hair.

Figure 2:
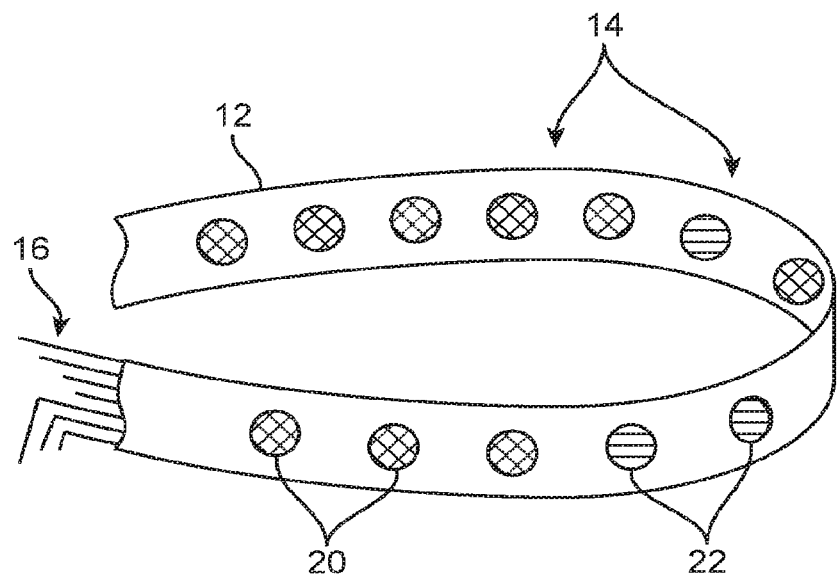
FIG. 2 illustrates a perspective view of one variation of the electrode carrier system where individual electrodes may be configured to indicate whether adequate contact is made with the underlying skin surface.

In one variation of the electrode carrier system 10, FIG. 2 illustrates a perspective view where each of the electrodes 14 may be configured to include a visual or haptic indicator to provide feedback to the user that sufficient electrode connection with the skin surface has been achieved. For instance, each electrode 14 may incorporate an impedance sensor and indicator such that when the controller and/or output device 18 detects a relatively low impedance, e.g., 5 kΩ, in a particular electrode 14, that electrode may be actuated to indicate that sufficient electrical contact between the electrode 14 and underlying skin is achieved.

FIG. 2 shows an example where each of the electrodes 14 may also incorporate visual indicators such as one or more light emitting diodes (LEDs). When sufficient electrical contact is achieved, the LED on a particular electrode 14 may emit a light of a first color 20, e.g., green, but if an electrode 14 has not achieved sufficient electrical contact, it may emit a light of a second color 22, e.g., red. Alternatively, a single color LED may be used where sufficient contact may be indicated by steady illumination of the LED and insufficient contact may be indicated by a blinking LED. In other variations, an electrode may include, e.g., a piezoelectric transducer, eccentrically loaded weight coupled to a motor, etc., to provide for a vibration or other haptic response to indicate whether the electrode 14 has sufficient electrical contact with the underlying skin. In this manner, the electrodes 14 may efficiently provide direct indication of electrical contact rather than having to review a separate controller or indicator.

Figure 3:
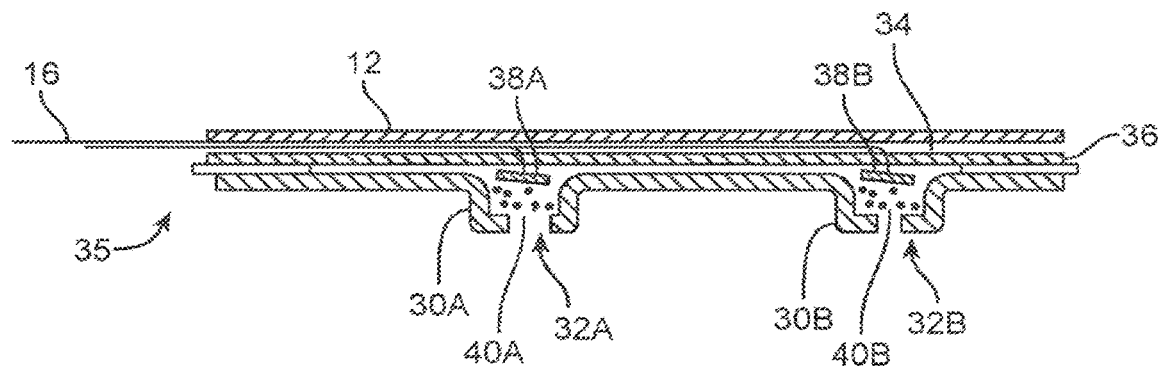
FIG. 3 illustrates a detail cross-sectional side view of another variation of the electrode carrier system where each of the electrodes may be encased or surrounded by a pressure release reservoir.

Turning now to the electrode configurations, FIG. 3 illustrates a cross-sectional detail side view of one variation of an electrode carrier system 35 where the electrodes 32A and 32B may be enclosed within a reservoir which is pre-filled with a conductive gel or fluid. Each electrode 38A, 38B may be configured into a flattened or atraumatic configuration which is contained within a respective reservoir 30A, 30B and each reservoir 30A, 30B may be formed of any number of flexible materials, e.g., silicone, polyurethane, rubber, etc., which can readily collapse. The electrodes 38A, 38B may be coupled via conductive wires 16 passing through a lumen 34 defined through the backing 12 separated from the electrodes by a substrate 36. Each reservoir 30A, 30B may also respectively define one or more openings 32A, 32B through which the conductive gel or fluid may be expelled.

Once the platform 12 has been situated over the patient's head H, the user may press upon each of the reservoirs 30A, 30B such that the conductive fluid or gel 40A, 40B flows through the openings 32A, 32B and onto the skin of the patient P. The conductive fluid or gel 40A, 40B expelled through the openings may maintain fluid communication between the skin surface and the respective electrodes 38A, 38B such that the detected electrical signals may be transmitted from the skin and to the electrodes 38A, 38B. Moreover, because of the flexibility of the reservoirs 30A, 30B, once the conductive fluid or gel 40A, 40B has been expelled into contact with the skin surface, the backing 12 may lie flat against the skin surface so that the patient P may comfortably lay their head upon a surface while still maintaining electrical contact with the electrodes 38A, 38B.

Figure 4:
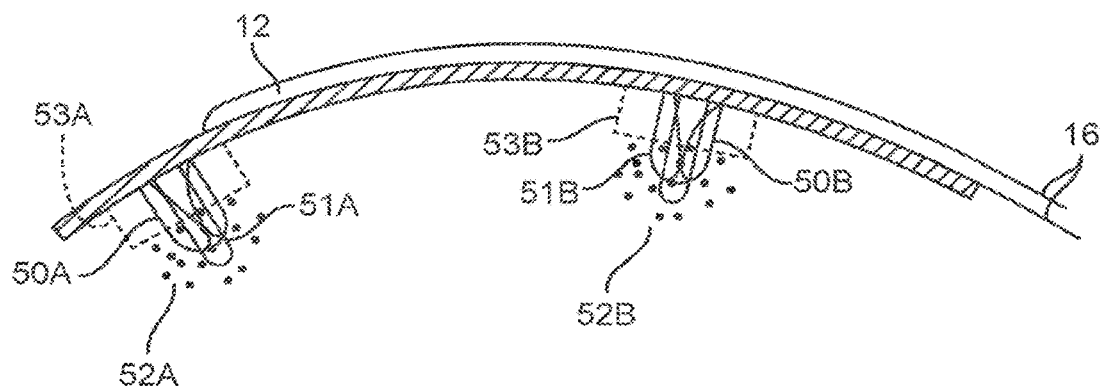
FIG. 4 illustrates a detail cross-sectional side view of another variation where the electrodes may be formed by one or more loops of conductive wire or ribbons.

FIG. 4 shows a side view of another electrode carrier system 35 where a pair electrode assemblies 50A, 50B may include one or more loops of conductive wire or ribbon 51A, 51B which are able to readily bend or flex against a skin surface. Some or all of the electrode assemblies 50A, 50B may include a pressure release reservoir (shown in broken lines 53A and 53B) for containing a conductive fluid or gel 52A, 52B, as described above, around each of the wire or ribbon electrodes 51A, 51B so that the conductive fluid or gel 52A, 52B may be expelled around and within the one or more loops to ensure a conductive path between the loops and the scalp. Alternatively, rather than using the pressure release reservoir, an amount of conductive fluid or gel may be simply placed upon the electrode assemblies 50A, 50B prior to placement against the patient's skin surface. Each of the wire or ribbon electrodes 51A, 51B may be electrically connected via conductive wires 16, and because the wire or ribbon electrodes 51A, 51B will preferably have a thin diameter or width, they may easily pass through the patient's hair and into contact with the scalp surface even when they bend or flex.

Figure 5:
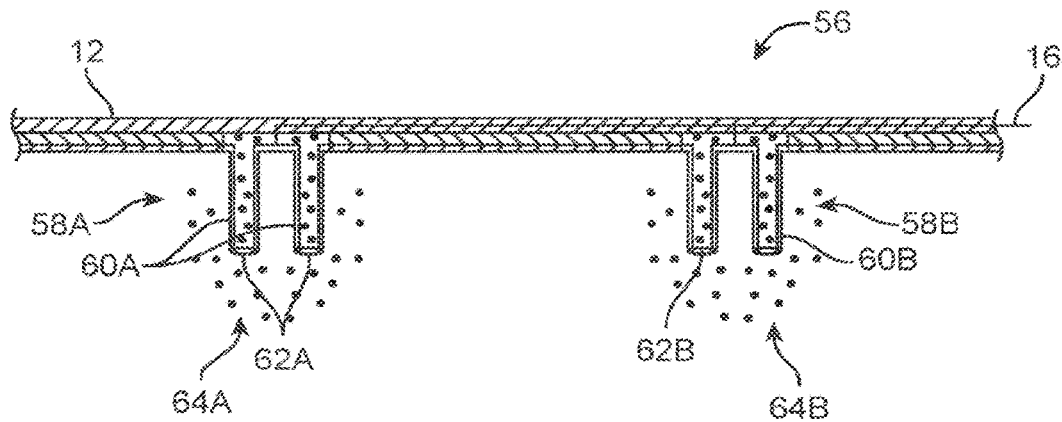
FIG. 5 illustrates a detail cross-sectional side view of another variation where each of the electrodes may be formed by one or more conductive tubes which define conduits.

FIG. 5 shows a side view of another variation of an electrode carrier system 56 having a plurality of electrode assemblies 58A and 58B each of which may include one or more tubular members 60A, 60B which may extend perpendicularly or at an angle from an inner surface (the surface that contacts the patient's scalp) of the backing 12. The tubular members 60A, 60B may define a lumen therethrough with an opening 62A, 62B defined at each distal end. Each of the tubular members 60A, 60B may be fabricated from a conductive metal which may retain its tubular shape when in use or which may be sufficiently thin and flexible to bend or yield when placed against the patient's skin surface. Alternatively, the tubular members 60A, 60B may be fabricated from a flexible material which is coated or layered with a conductive material such that the members retain their flexibility. In either case, a conductive fluid or gel 64A, 64B may be either contained within the tubular members 60A, 60B or they may be retained within a pressure release reservoir, as described above but not shown in FIG. 5, surrounding or in proximity to each electrode. Because the tubular shape of the electrodes, they may readily pass through the patient's hair, if present, and into contact against the skin surface while maintaining electrical contact. The tubular members 60A, 60B may be arranged in tandem pairs, as shown, or may be arranged in a triangular, rectangular or circular pattern when there are three, four, or more tubular members in a single electrode assembly 58A, 58B.

Figure 6A:
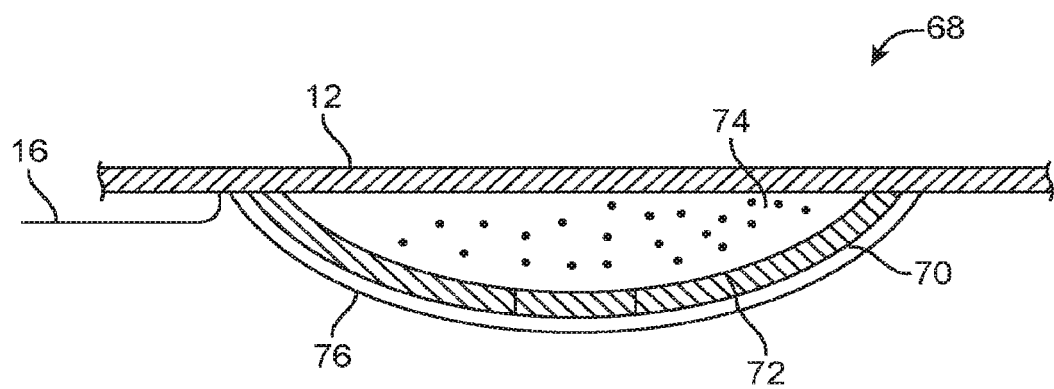
FIGS. 6A to 6C illustrate cross-sectional side views of yet another variation where each electrode may include a compressible reservoir having one or more openings.
Figure 6B:
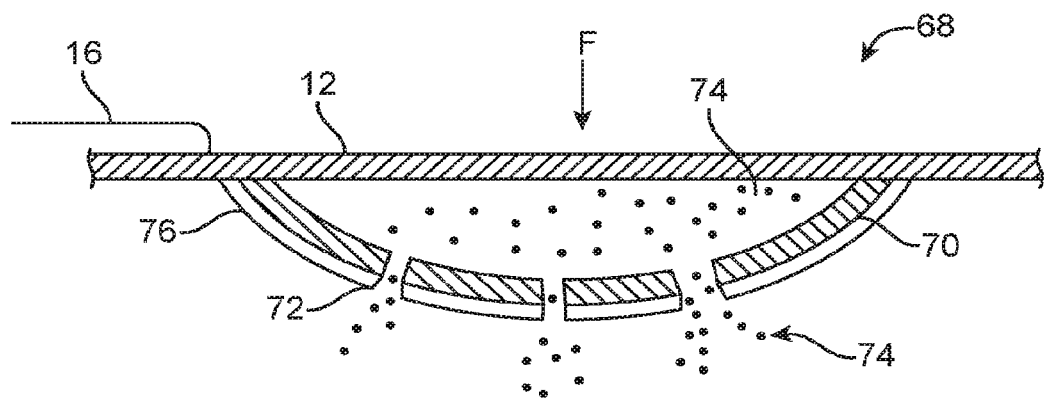
Figure 6C:
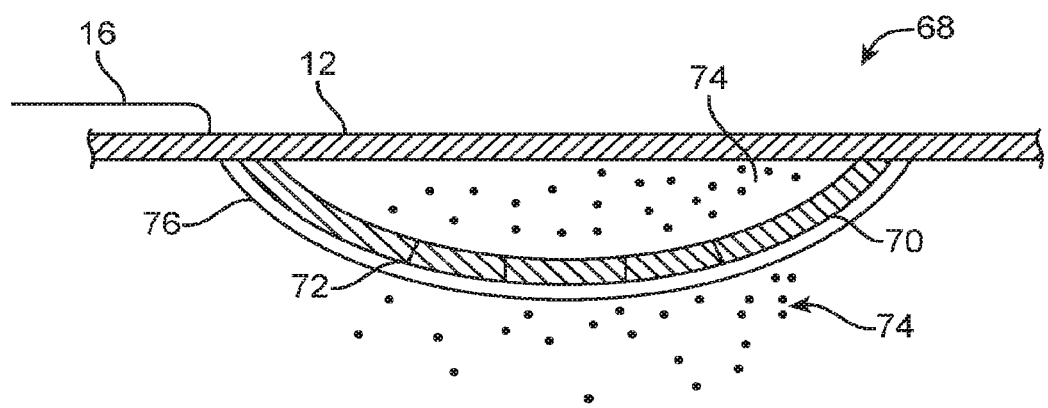

Referring to FIGS. 6A-6C, a further embodiment of an electrode carrier system 68 includes a pressure release reservoir 70 filled with a conductive fluid or gel 74. The reservoir 70 may be formed of a flexible material, e.g., silicone, polyurethane, rubber, etc., and extends from a backing 12 to form a curved or arcuate structure with one or more openings 72 defined over an interior of the reservoir 70. These openings 72 typically remain in a closed state until a force F is applied to the reservoir 70 and/or backing 12 to cause an electrically conductive fluid or gel 74 contained within the interior of the reservoir to escape through the openings 72, as shown in FIG. 6B, and into contact with an outer surface of the reservoir 70 and form an electrically conductive path to underlying skin surface. A layer of conductive material 76 is electrically coupled to conductive wire(s) 16 and may be formed over a portion or the entire outer surface of the reservoir 70. Electrical contact with the skin surface may be achieved by applying force F to the backing 12 or reservoir 76, as shown in FIG. 6B, to extrude or otherwise release the fluid or gel 74 from the interior of the reservoir 70 and out onto the conductive material 76 and skin as shown in FIG. 6C, where the openings 72 return to their closed state after the force F is removed.

Figure 7A:
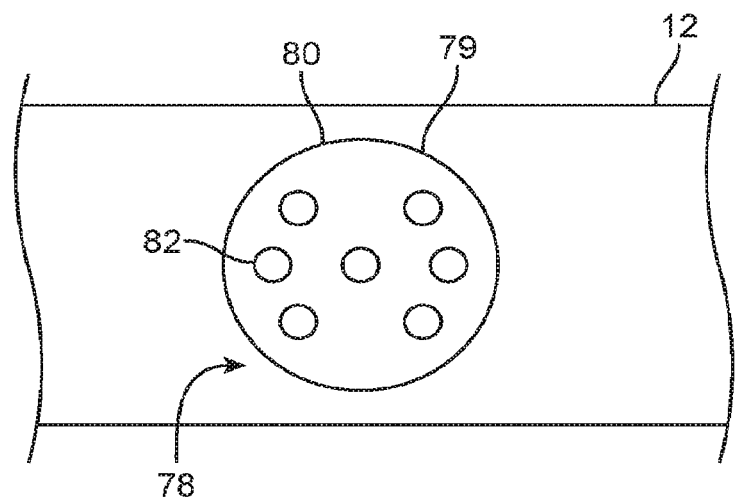
FIGS. 7A and 7B illustrate top and partial cross-sectional perspective views of another variation where each electrode is formed to have one or more conductive tubes in fluid communication with a compressible reservoir.
Figure 7B:
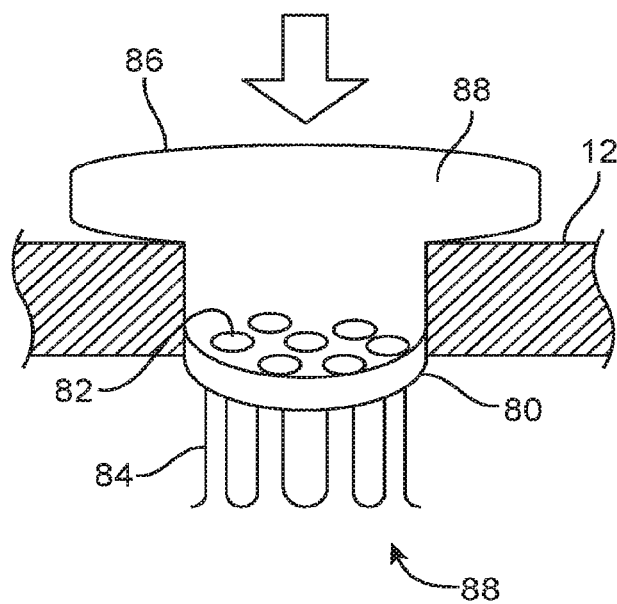

Referring to FIGS. 7A-7B, a still further embodiment of an electrode carrier system 78 includes of an electrode assembly 79 having an electrode body 80 which carries one or more tubular members 84 extending from a lower surface thereof. The tubular members 84 project perpendicularly away from a plane of the backing 12. In some embodiments, the electrode body 80 will be formed at least partially from a conductive material, such as a rigid or flexible metal, and/or a conductive polymer, such as a conductive silicone. In other embodiments, the electrode body 80 will be formed at least partly from a non-conductive flexible material, e.g., silicone, polyurethane, rubber, etc., which may be coated or layered with a conductive material such that at least the tubular members 84 are electrically conductive while retaining their flexibility. Because of the conductivity, the electrode body 80 and tubular members 84 may be electrically coupled directly to the conductive wires or ribbons.

In both cases, the electrode body 80 may be secured to the backing 12 such that the tubular members 84 extend through an opening in the backing so that they can contact the patient's scalp when the backing is placed over the head, e.g. as shown in FIG. 1. An electrically conductive fluid or gel 88 is contained in an interior reservoir 86 of the electrode body 80 and can be delivered through passages in the tubular members by pressing on a flexible top of the electrode body as indicated by the arrow in FIG. 7B.

The tubular members 84 may be arranged in a uniform or an arbitrary pattern and are in a generally circular pattern as illustrated in FIGS. 7A and 7B. After the backing 12 has been secured to the patient, the reservoir 86 may be pressed or urged such that the fluid or gel 88 contained within is expelled through central passages along the lengths of each of the tubular members 84 and into contact against the underlying skin surface through corresponding distal openings. The members 84 will typically be elongated, e.g., having a length in the range from 1-2 cm, and may to pass readily through the patient's hair, if present, and into direct contact against the skin surface. Moreover, even with the tubular members 84 in a collapsed or deformed configuration, e.g. when the patient lays their head down, the tubular members 84 and body 80 may continue to conduct the electrical signals from the underlying skin surface.

Referring now to FIG. 8, a still further embodiment of an electrode carrier system 89 includes a tubular body 90 which may define one or more openings 96 over its surface. The tubular body 90 may have one or more tubular members 92 which extend in a spiral or helical pattern away from the backing 12. The one or more tubular members 92 may each define a lumen therethrough which extends from a bottom of the tubular body 90 and to a distal opening 94 at its tip. The backing 12 may further define a reservoir 100 which contains a volume of conductive fluid or gel 102 such that the body 90 is in fluid communication with the reservoir 100. Opposed walls 104A, 104B may enclose the reservoir, and one or both of the walls 104A, 104B may be squeezed or otherwise translatably moved toward the tubular body 90. Alternatively or additionally, the body 90 may be rotatably secured to the backing 12 such that the body 90 and members 92 may be rotated about its longitudinal axis as indicated by 98 to distribute the conductive fluid or gel 102 and exfoliate the skin to promote electrical contact between the electrically conductive tubular members 92 and the scalp.

Additionally and/or alternatively, the distal tips 94 of the members 92 may present a roughened surface for contacting the skin. The optionally roughened tips may be rotated upon the skin surface by the user to at least partially exfoliate the skin surface to facilitate electrical contact.

When in use, once the backing 12 has been secured to the patient's head, the tubular body 90 may be rotated manually by the user such that the members 92 are advanced into and through any hair which may be present upon the patient's scalp. Once the openings 94 of the distal tip are positioned in contact with or proximity to the skin surface, one or both walls 104A, 104B may be actuated, e.g., squeezed by the user, such that the conductive fluid or gel 102 is introduced within the interior of the tubular body 90 via the openings 96. The conductive fluid or gel 102 may flow into the tubular body 90 and within the members 92 and out through the openings 94 and into contact upon the skin surface.

As described above, the tubular body 90 and/or members 92 may be fabricated from a conductive material which is also flexible, e.g., conductive silicone, and/or from a flexible material, e.g., silicone, polyurethane, rubber, etc., which may be coated or layered with a conductive material such that the underlying tubular body 90 and/or members 92 retain their flexibility. Because of the conductivity, the tubular body 90 may be electrically coupled directly to the conductive wires or ribbons. Furthermore, with the tubular body 90 and/or members 92 having an optionally flexible configuration, the members 92 may collapse upon themselves while retaining electrical conductivity with the underlying skin surface.

Turning now to other aspects of the present invention, the electrode carrier system may also be utilized for other applications such as patient motion tracking employing either visual motion tracking or accelerometers.

Figure 9:
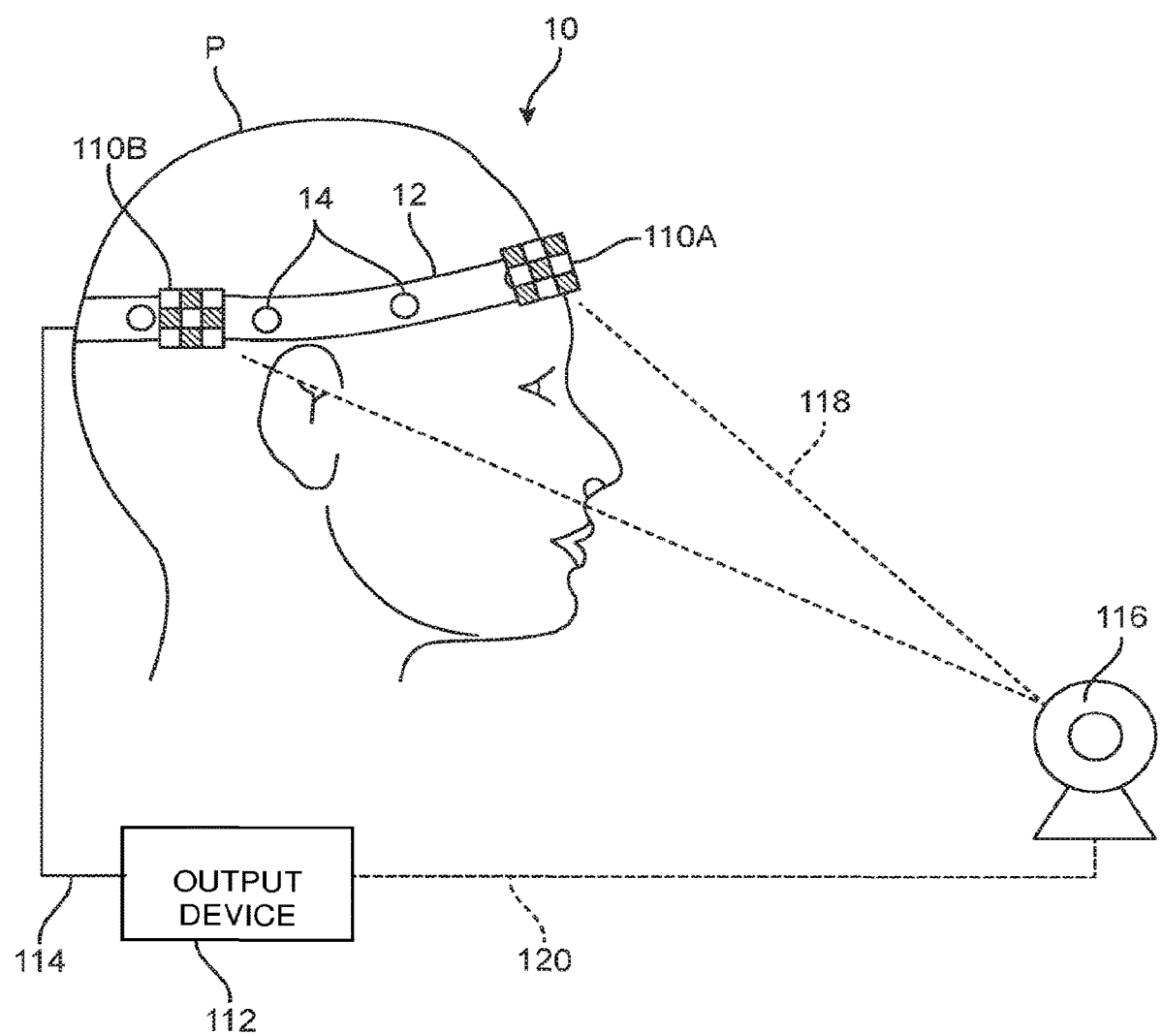
FIG. 9 illustrates an example of optically tracking the movement of a patient in combination with the electrode carrier system.

In further embodiments, the electrode carrier system may be configured as a headband, as illustrated in FIG. 9, and fitted upon a patient P. The electrode carrier system is in electrical communication with a controller and/or output device 112 via conductive wires 114. In other variations, the device 112 may be coupled wirelessly as well. The electrode assemblies 14 may incorporate any of the electrode assembly variations described herein and in any number of combinations, if so desired. In the embodiment illustrated in FIG. 9, the headband backing 12 may further incorporate one or more fiducial markers 110A, 110B which allow for the visual tracking of these markers 110A, 110B within the field of view of a camera or other optical imager 116. The markers 110A, 110B may include any variety of visual indicators shown in this variation as high-contrast printed patterns having specified shapes, as shown. In other variations, the fiducial markers 110A, 110B may include lights such as an arrangement of LEDs.

While two markers are illustrated as an example, additional markers may be further distributed around the circumference of the backing 12 to allow for more precise tracking, e.g., to allow for tracking when the patient's head H may be turned in a manner which obscures one of the markers. As noted, a camera or other optical imager 116, such as a digital camera, may be positioned in proximity to the patient P during use of the electrode carrier system 10 such that the electrode carrier system 10 and markers 110A, 110B remain in the field of view 118 of the imager 116. While a single imager 116 is shown in this example, additional imagers positioned at different locations may also be used in combination to help ensure that the electrode carrier system 10 and markers 110A, 110B remain in the field of view 118 at all times. Additionally, the imager 116 may be optionally motorized with pan and tilt capabilities to ensure that the patient P remains in the field of view 118 of the imager 116.

With the electrode carrier system 10 electrically coupled to the controller and/or output device 112, the imager 116 may also be connected to the controller and/or output device 112 by wires or another communications link 120 or to a second controller and/or output device through wired or wireless communication. In this manner, the controller 120 may be further programmed with a computer vision algorithm to identify a position and orientation of the patient's head H so that the controller may receive the marker information from imager 116 to determine patient movement in real time. This information can then be used for artifact rejection and diagnostic purposes. For instance, visual tracking of the markers 110A, 110B may be used to determine or confirm whether the patient P is experiencing a convulsive seizure particularly if the patient's detected brain signals are sonified.

Figure 10:
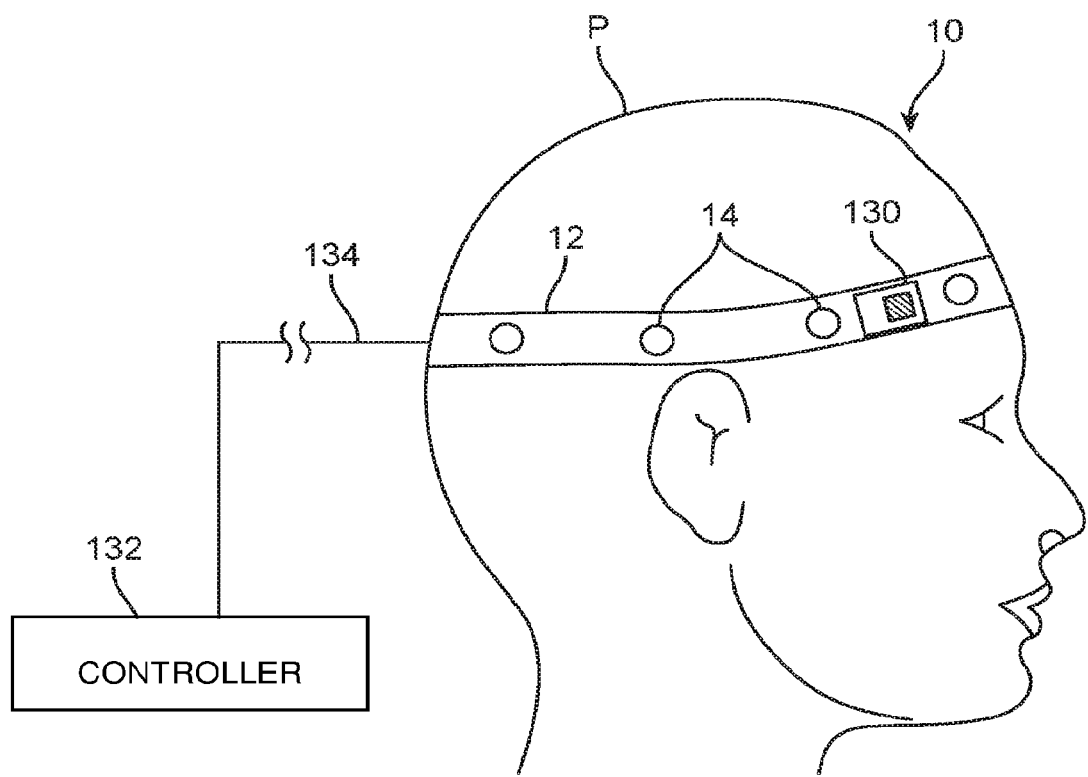
FIG. 10 illustrates another example of utilizing one or more accelerometers for detecting the patient's movements in combination with the electrode carrier system.

In yet another variation, instead of visual markers, the electrode carrier system 10 may incorporate one or more accelerometers 130 attached within or along the backing 12, as shown in FIG. 10. The one or more accelerometers 130 may comprise three-axis accelerometer devices which are sensitive enough to detect the movement of the patient's head. This data can be transmitted to the controller and/or output device 132 via conductive wires 134 for processing to determine the patient's movements as well as motion artifact rejection. If the detected acceleration exceeds a predetermined threshold, this may be an indicator to the controller that these motion artifacts may be excluded from consideration to prevent the inclusion of artifact noise from other detected data.

The electrode carrier system 10 may be utilized with any combination of electrodes described herein and may also be used in any combination with either the optical motion detection or accelerometer monitoring. In other variations, both the optical motion detection and accelerometer monitoring may be utilized in combination together, if so desired.

Figure 11:
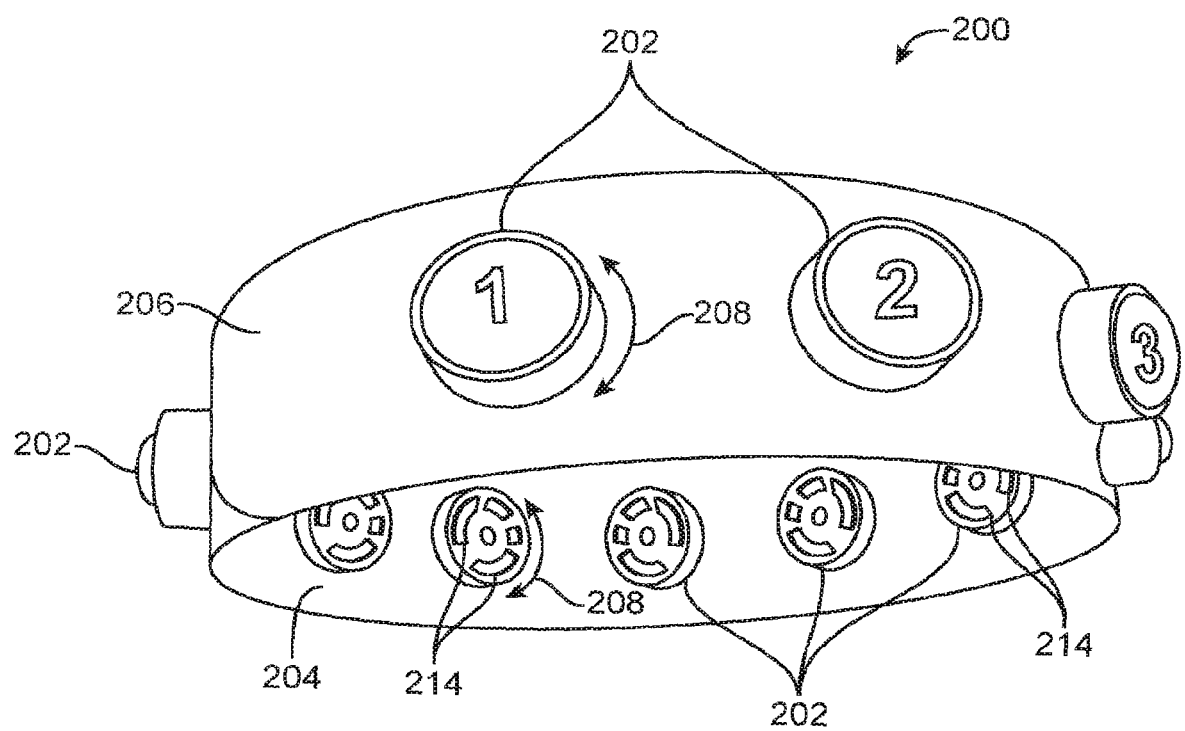
FIG. 11 illustrates an electrode carrier system of the present invention comprising a headband having a plurality of electrode assemblies distributed over a length thereof.
Figure 12:
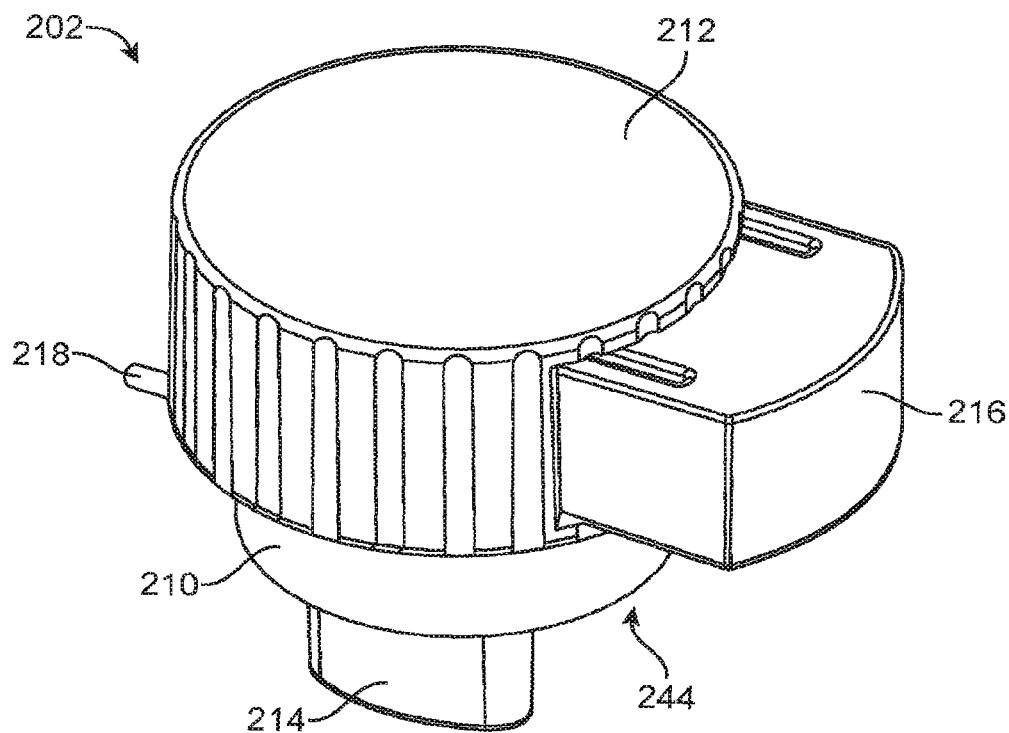
FIG. 12 illustrates an exemplary electrode assembly constructed in accordance with the principles of the present invention.
Figure 13:
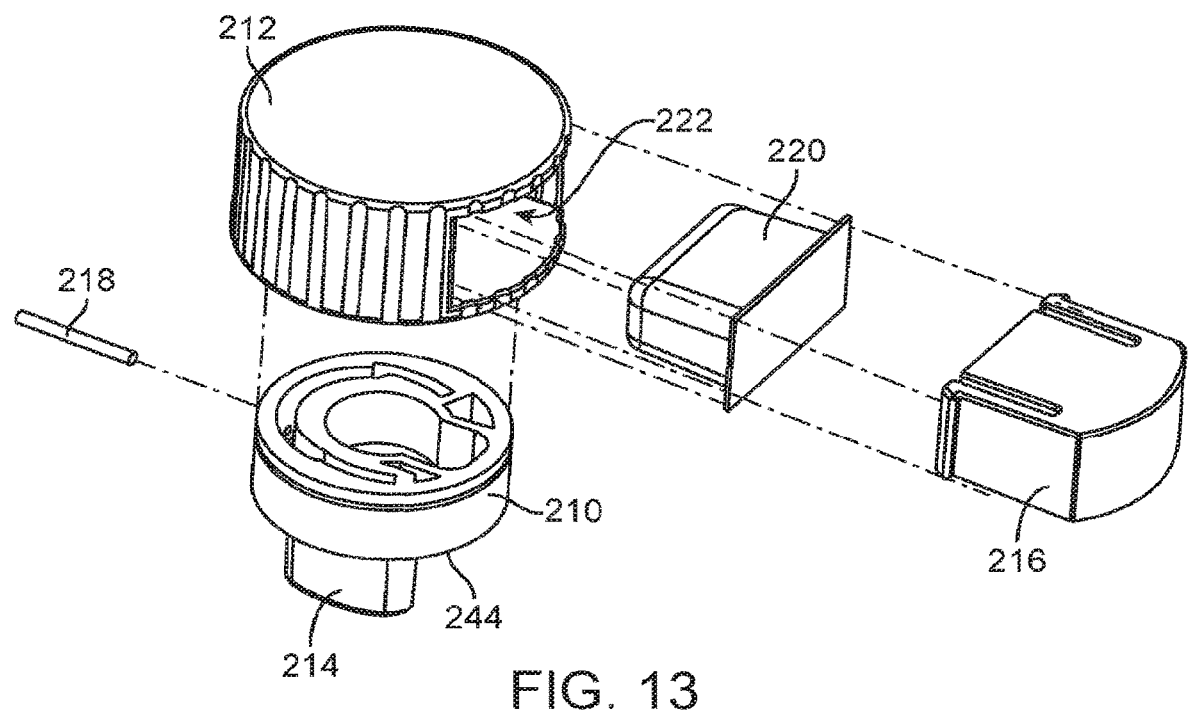
FIG. 13 illustrates the electrode assembly of FIG. 12 shown in an exploded view.
Figure 14:
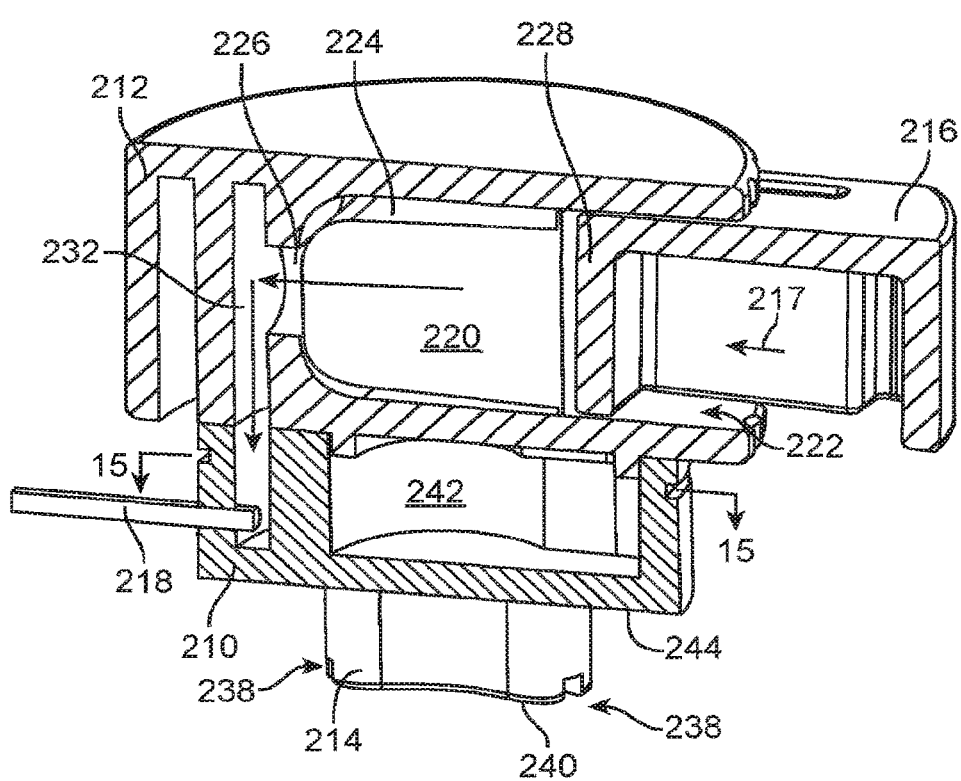
FIG. 14 illustrates the electrode assembly of FIG. 12 shown in a cross-sectional view.

Referring now to FIG. 11, an electrode carrier system 200 constructed in accordance with the principles of the present invention includes an elongated backing 204, typically in the form of a headband or other headgear, having a plurality of electrode assemblies 202 distributed along a length thereof. The elongated backing 204 will typically have overlapping ends 206 which may be adjustably attached when the elongated backing is placed over a patient's head, generally as shown in FIG. 1 above. The overlapping ends may be attached using any conventional method, such as with Velcro® hook and loop fasteners.

The electrode assemblies 202 are preferably rotatably mounted so that a user can manually rotate them back and forth as shown by arrows 208 so that the patient's skin can be gently abraded after the elongated backing has been placed over the scalp. In particular, it will be desirable to perform such manual abrasions immediately prior to dispensing the electrically conductive fluid or gel as will be described in more detail here and below. In other instances, the abrasion can be performed while dispensing the electrically conductive fluid or gel and/or after dispensing the electrically conductive fluid or gel.

Referring now to FIGS. 12-16, the electrode assemblies 202 will typically include a lower body portion or base 210, an upper body portion or cap 212, and one or more tubular members 214 depending downwardly from a bottom surface 244 of the lower body portion. A plunger 216 is configured to enter a chamber 224 within the upper body portion 212 through an opening 222. A sealed dispensing container, such as a cartridge or sealed dispensing container 220 holds the electrically conductive fluid or gel and is configured to be constrained within the chamber 224 while the plunger 216 extends readily outwardly from the upper body portion 212, i.e. is in its non-depressed configuration.

Figure 15:
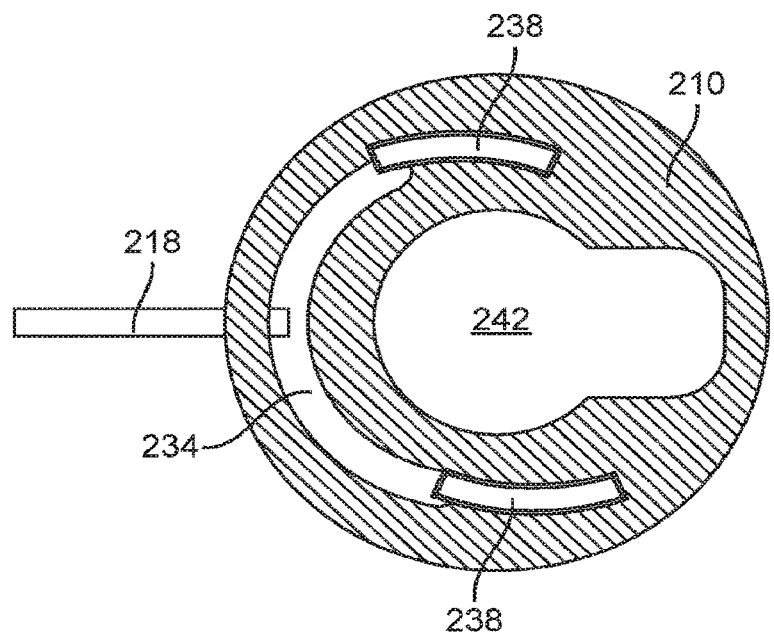
FIG. 15 shows a cross-sectional view of a lower portion of the electrode assembly of FIGS. 12-14 taken along line 15-15 of FIG. 14.
Figure 16:
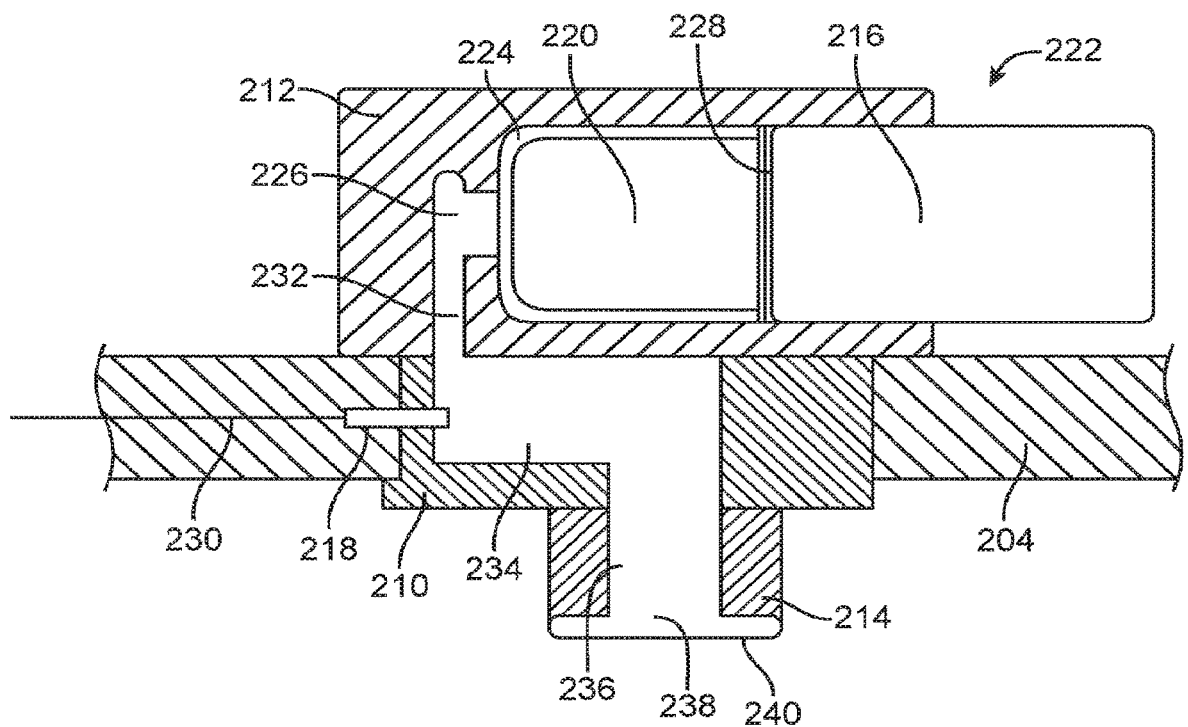
FIG. 16 is simplified illustration of the electrically conducted fluid or gel flow path within the electrode assembly of FIGS. 12-15 where the specific components and flow path segments use the numbering employed in FIGS. 12-15.

Once the sealed dispensing container 220 is placed in the chamber 224, the plunger 216 can be positioned so that a leading edge 228 is adjacent one side of the sealed dispensing container. By pressing the plunger 216 in the direction of arrow 217, the electrically conductive fluid or gel within the sealed dispensing container 220 will be pressurized causing a portion of the container to pass through the dispensing hole 226. As additional pressure is applied with the plunger 216 the portion of the chamber within the dispensing hole 226 will rupture and cause the electrically conductive fluid or gel to flow into a vertical passage 232 within the upper body portion 212, as in FIGS. 14 and 16. The electrically conductive fluid or gel will then come in contact with the electrically conductive terminal 218, and the electrically conductive fluid or gel will continue to flow through a horizontal passage 234 and on to vertical lumens 238 within the prongs 214, as seen in FIGS. 15 and 16.

After flowing through the vertical lumen 238, the liquid or gel will flow outwardly through channel 240 formed in the bottom of the prong 214 so that it may flow on to patient tissue in contact with the lower surface 240 of the prong. For completeness, it is noted that the lower body portion or base 210 has a hollow interior 242 which is an artifact of manufacturing and which does not play a direct role in fluid flow within the device.

Once the entire flow path from the vertical passage 232 through the channel 238 in the lower surface of the prong 214 is filled with electrically conductive fluid or gel, it will be appreciated that biological electrical current present in the region of the liquid or gel will be conducted to the electrically conductive terminal 218 which in turn is connected to a wire or other conductor 230 present in the backing 204 of the electrical carrier system 200. For completeness, it is noted that the attachment of the wire 230 or other conductor to the electrically conductive terminal 218 will be made in such a fashion that it can accommodate rotation of the electrode assembly relative to the elongated backing 204, as shown by arrow 208 and FIG. 11.

Figure 17:
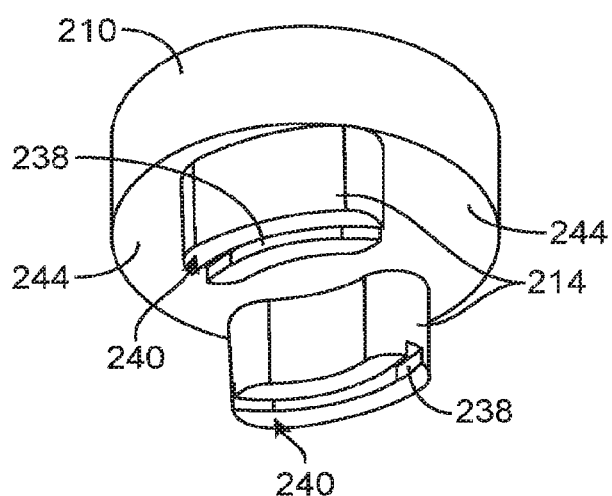
FIGS. 17 and 18 are detailed views of a bottom portion of the electrode assembly of FIGS. 12-15.
Figure 18:
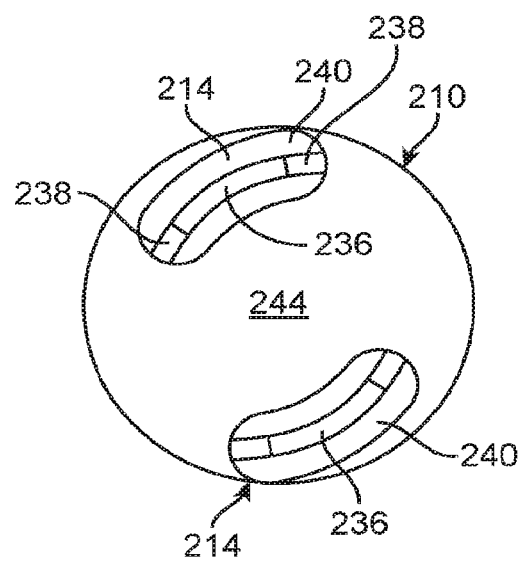

Referring now to FIGS. 17-27, a variety of different configurations for the lower body portions of the electrode assemblies of the present invention will be described. FIGS. 17 and 18 illustrate the lower body portion 210 which has been shown in connection with FIGS. 12-16 above. The detailed views of FIGS. 17 and 18 show that a pair of prongs 214 are formed on the lower surface 244 of the lower body portion 210. As best seen in FIG. 18, the prongs 214 have generally crescent or arcuate shapes with curved channels formed on their lower surfaces 240. The curves or arcs of the prongs 214 are not, however, concentric with the circular periphery of the lower body portion 210. Instead, the arcs of the prongs 214 are non-concentrically positioned on the bottom 244 of the lower body portion 210. In this way, gel which enters from the vertical lumens 236 of the prongs will be dispensed from the tissue so that it will be distributed by the lower surfaces 240 of the prongs as the electrode assembly 202 is rotated back and forth as discussed previously. Thus, this asymmetry of the prongs will help promote distribution of the electrically conductive fluid or gel as it is dispensed through the vertical lumens 236 and arcuate channels 238.

Figure 19:
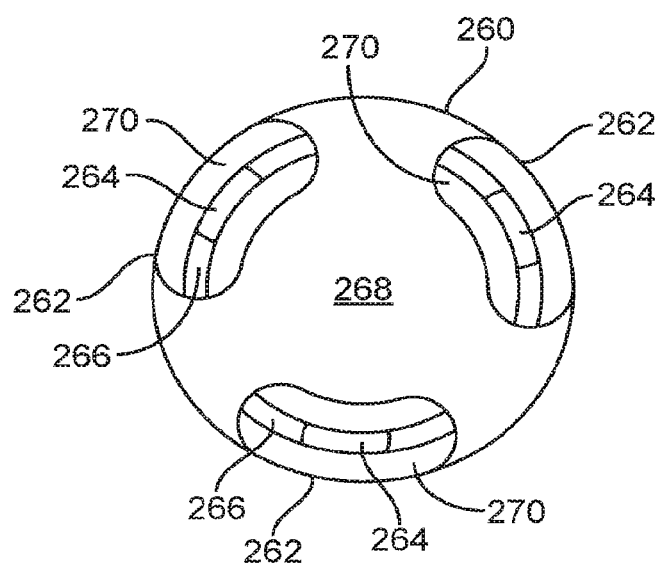
FIGS. 19 and 20 illustrate an alternative bottom portion which could be substituted for the bottom portion illustrated in FIGS. 12-15.
Figure 20:
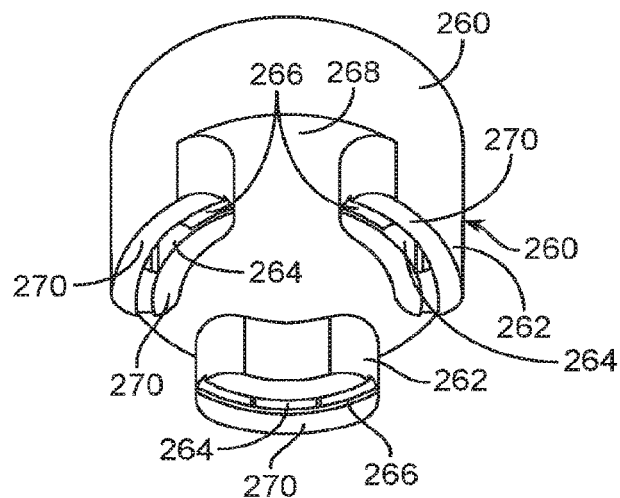

In an alternative embodiment, a lower body portion or base 260, as illustrated in FIGS. 19 and 20, has three prongs 262 which are concentrically and evenly distributed about the bottom 268. Thus, electrically conductive fluid gel which is delivered through vertical lumens 264 and distributed through channels 266 formed in the lower surfaces 270 of each prong will not be further distributed by passage of the lower surfaces over the gels. The presence of three prongs, however, will further promote reliable electrical connection.

Figure 21:
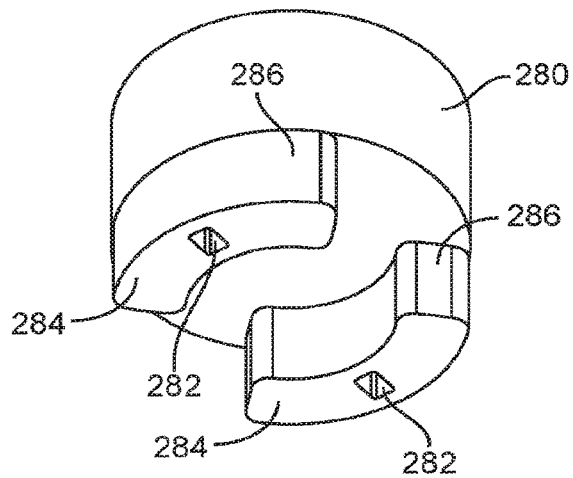
FIGS. 21-27 each illustrate a further alternative configuration of a bottom portion of an electrode assembly constructed in accordance with the principles of the present invention.
Figure 22:
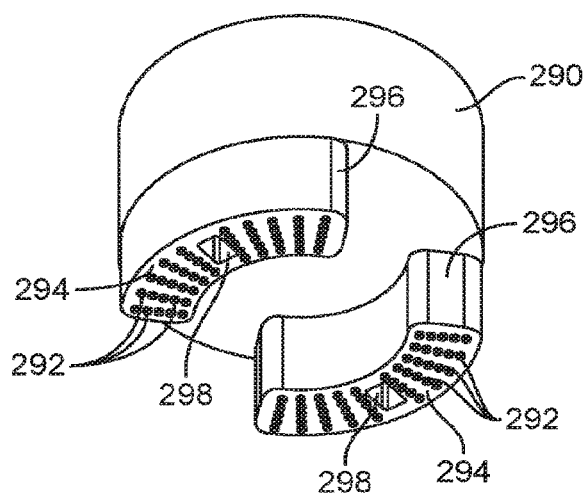
Figure 23:
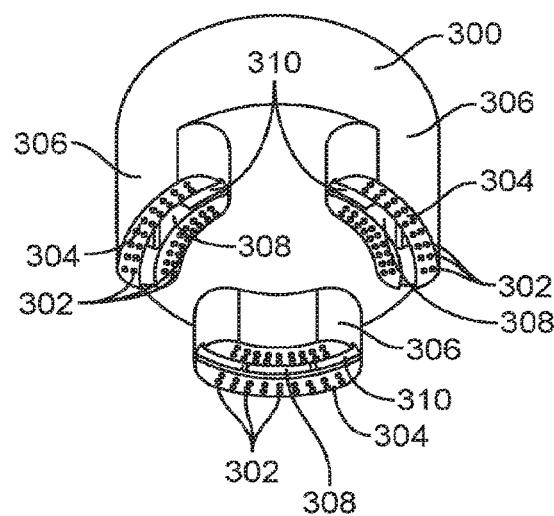

Referring now to FIG. 21, an additional embodiment of a lower body portion 280 includes two symmetric prongs 286 having single flush ports 282 in the lower surfaces 284 thereof. However a similar lower body portion 290 having three prongs 296 come each with a lower surface 294 having a flush port 98 therein further includes the plurality of surface features 292, typically in the form of small bumps, which help distribute the electrically conductive fluid or gel which is being distributed through the ports 298.

A further embodiment of a lower body portion or base 300 having three symmetric prongs 306 is illustrated. Each prong 306 has a lower surface 304 with a plurality of surface features 302 formed thereon. The prongs, as with prior embodiments, each have vertical lumens 308 opening to channels 310 formed in the lower surfaces for delivering and distributing electrically conductive fluids or gels.

Figure 24:
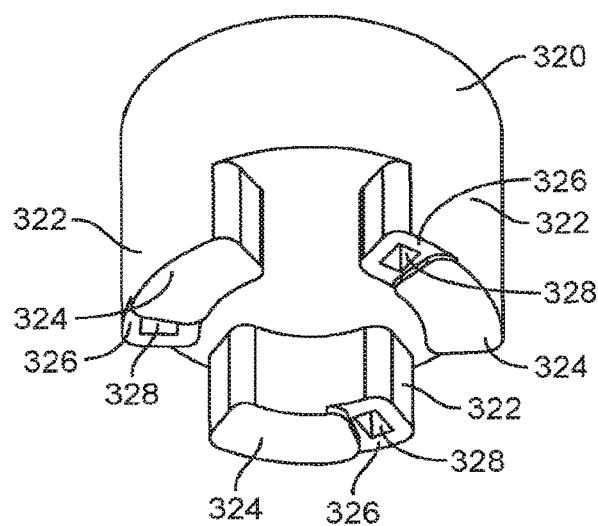

Still further alternative embodiments of bottom portions of the electrode assemblies of the present invention are shown in FIGS. 24 through 27. Instead of having a single lower surface on each prong with a channel of port form therein, these lower body portions have lower surfaces with a recess for delivering the electrically conductive fluid or gel. As shown in FIG. 24, a bottom portion 320 includes three symmetrically placed prongs 322 extending from the bottom thereof. Prongs each have lower surfaces 324, but the fluid or gel delivery ports 328 are formed in recessed surfaces of the prongs.

Figure 25:
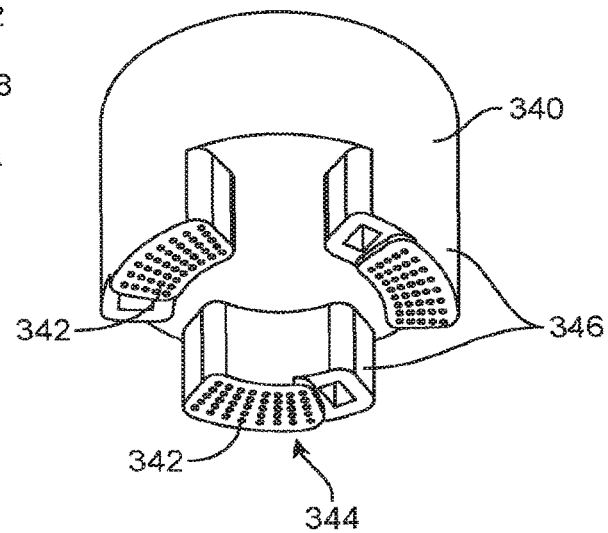

FIG. 25 shows a similar bottom portion 340 having three asymmetric prongs 342 where the lower surfaces 344 of each prong comprise a plurality of surface features 342.

Figure 26:
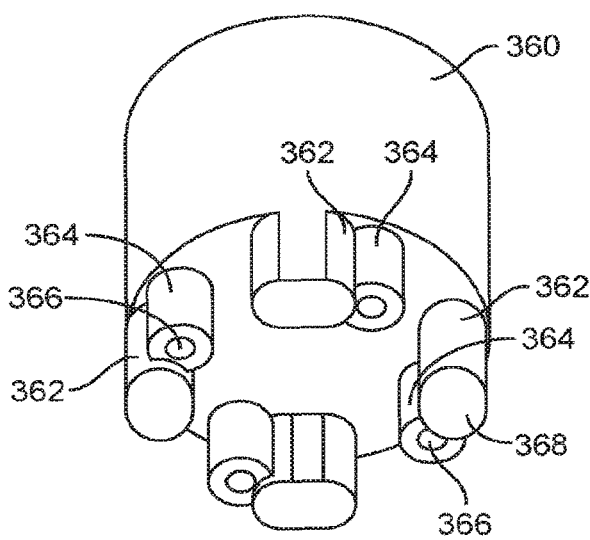

An alternative lower body portion 360, as illustrated in FIG. 26, comprises prongs 362 having adjacent gel or fluid delivery tubes 364 with ports 366 therein. The prongs 362 have generally flat lower surfaces free from surface features.

Figure 27:
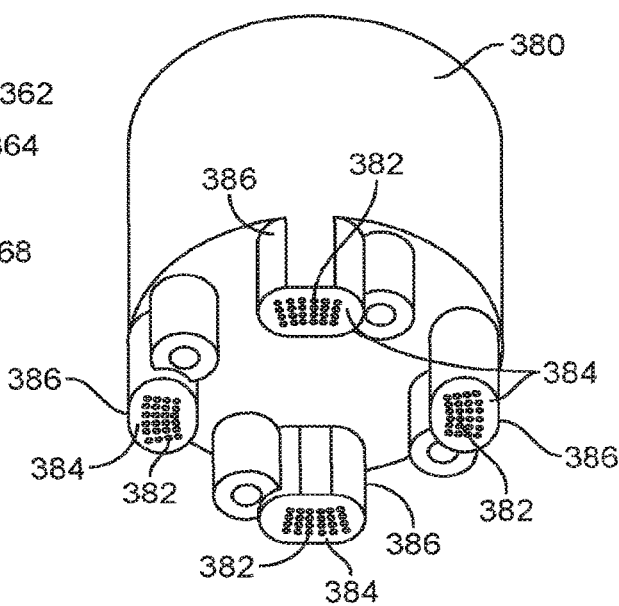

In FIG. 27, a lower body portion 380, similar to lower body portion 360, includes three prongs 386 having adjacent fluid delivery tubes. The lower surfaces 384 of each prong 386 include surface features 382.

Figure 28A:
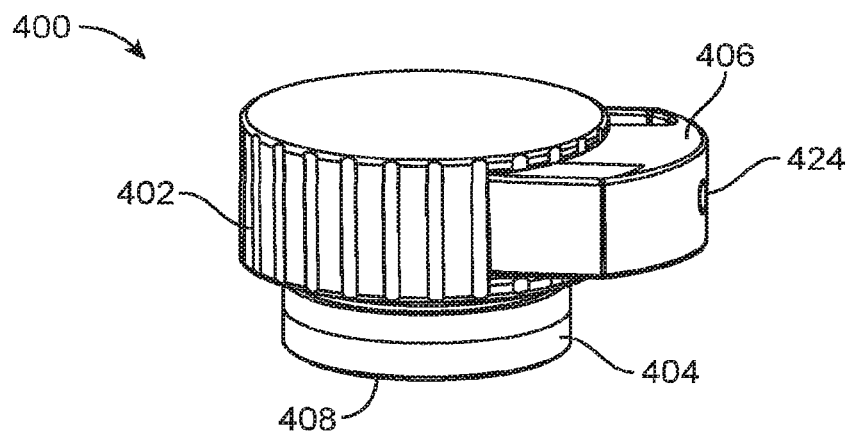
FIGS. 28A-28C illustrate yet another alternative configuration of a bottom portion of an electrode assembly having a flat surface which is free from tubular members and other similar structures.
Figure 28B:
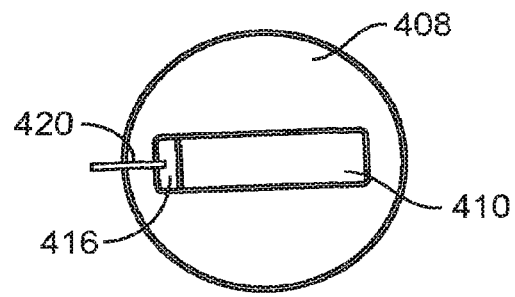
Figure 28C:
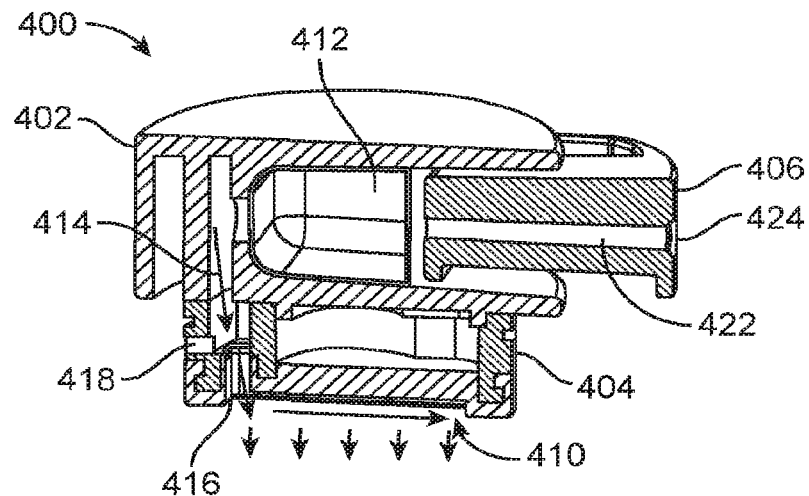

Referring now to FIGS. 28A-28C, an electrode assembly 400 comprises an upper portion or cap 402 and a lower portion or base 404. A plunger 406 is reciprocatably received through a wall of the cap 402 and extends into a reservoir 412, generally as described for previous embodiments. In contrast to previous embodiments, however, the lower portion or base 404 of the electrode assembly 400 has a flat bottom surface 408, as best seen in FIGS. 28B and 28C. The electrode assembly 400, which is free from tubular and other protruding elements on the bottom surface of its lower portion, is particularly useful for engagement against tissue surfaces which are free from hair, such as a patient's forehead. It will be appreciated, as described above, that the tubular members of the present invention are particularly intended to allow electrical contact to be made through a patient's hair present on a scalp. As a headband, for example headband 206 in FIG. 11, circumscribes the patient's skull, at least some of the electrode assemblies 202 will be engaged against the patient's forehead where there is little or no hair. In such instances, those electrode assemblies which engage the forehead can be made without tubular members as illustrated in FIGS. 28A-28C.

As with previous embodiments, the reservoir 412 of the electrode assembly 400 may have a capsule or other sealed container holding the electrically conductive gel or other fluid therein. Alternatively, the gel may be unconstrained within the reservoir 412, e.g. being introduced into the reservoir by injection through a passage 422 having a port 424 in the plunger 406. As the plunger 406 is depressed, pressure on the gel within reservoir 412 (either encapsulated or unconstrained) will cause the gel to flow downwardly through vertical passage 414 and out through a bottom port 416 into a slot 410 formed in the bottom surface 408. The gel or other electrically conductive fluid will be able to distribute within the slot and form an electrically conductive path with an electrically conductive terminal 420 which passes through a hole 418 in a wall of the lower portion or base 404. Thus, biological electrical signals may be coupled through the patient's skin into the electrically conductive gel in the slot 410 so that current may pass to the electrically conductive terminal 420. Optionally, the bottom surface 408 may be modified to enhance electrical conductivity in any of the ways described elsewhere herein in connection with other embodiments of the electrode assemblies.

Figure 29A:
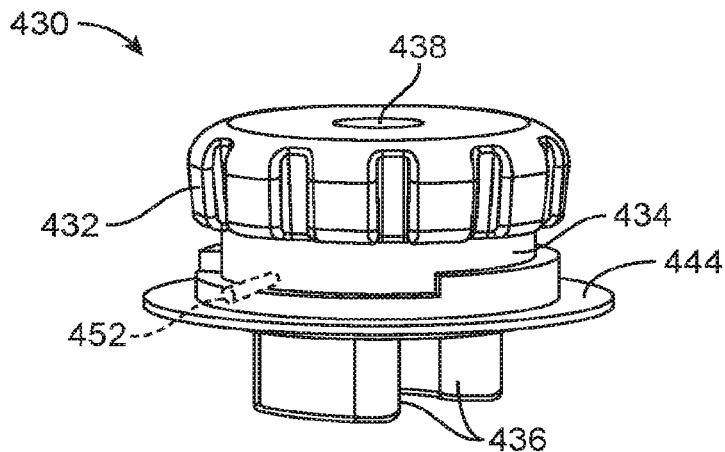
FIGS. 29A-29C illustrate a further exemplary electrode assembly constructed in accordance with the principles of the present invention having one or two grommets for attachment of the electrode assembly to a headband and further having a vertical passage for introducing an electrode gel using an assembly or other delivery device.
Figure 29B:
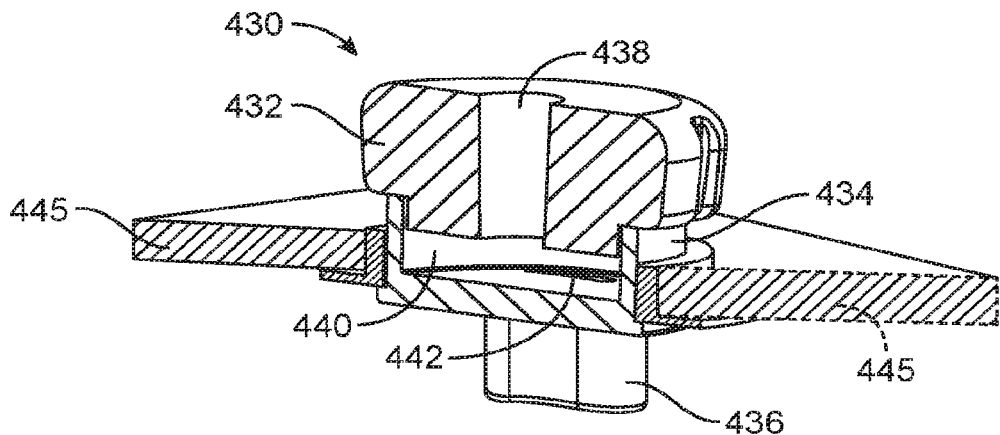
Figure 29C:
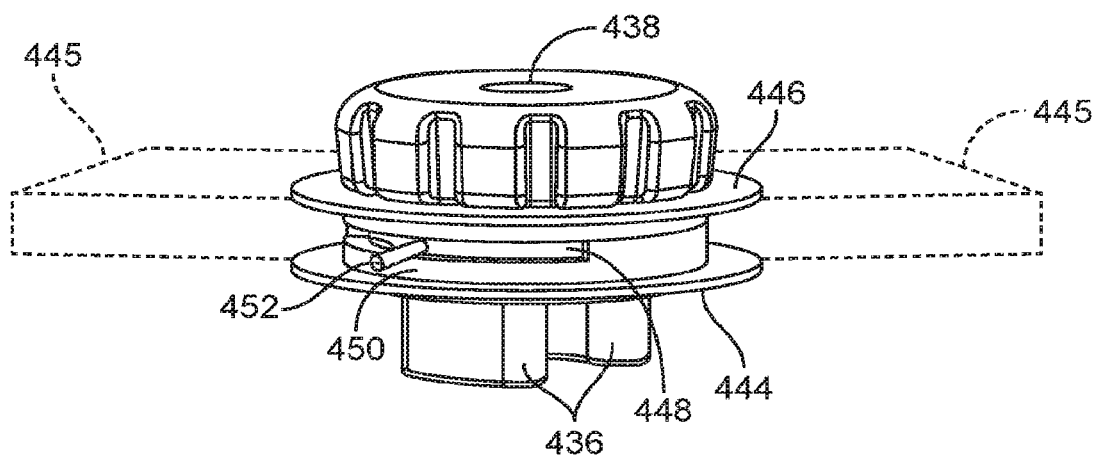

Referring now to FIGS. 29A-29C, an electrode assembly 430 constructed in accordance with principles of the present invention comprises an upper portion or a cap 432 and a lower portion or base 434. Tubular members or probes 436 project downwardly from a bottom surface of the lower portion or base 434, and a chamber 440 is formed in the lower portion or base to receive an electrically conductive gel or other fluid through a vertical passage 438 in the upper portion or cap 432. It will be appreciated that the electrode assembly 430 does not include a plunger for delivering the electrically conductive gel as with other embodiments described herein.

The electrically conductive gel or other fluid may be injected through the vertical passage 438, so that the gel flows first into chamber 44 and then through a vertical delivery passage 442 formed through the tubular member or probe 436. The electrically conductive gel or other fluid will thus be able to flow onto the patient's skin so that it can form an electrically path from the skin to an electrically conductive terminal or pin 452 which passes through the wall of the lower portion or base 434 into the chamber 440.

The electrode assembly 430 is mounted in a lower grommet 444 and optionally in an upper grommet 446. A single grommet 444 can be connected to a headband 445 using adhesives, staples, pins, or the like as shown in FIG. 29B. Alternatively, the headband 445 may be sandwiched between the upper and lower grommets 444 and 446, as shown in FIG. 29C. In such instances, at least one of the grommets will include a slot 448 to receive the electrically conductive terminal 452 and allow the electrode assembly to be rotated within the grommets 444 and 446. The slot allows the electrically conductive terminal 452 to move while the electrode assembly is being rotated to enhance electrical contact to the skin, as described elsewhere herein.

Figure 30A:
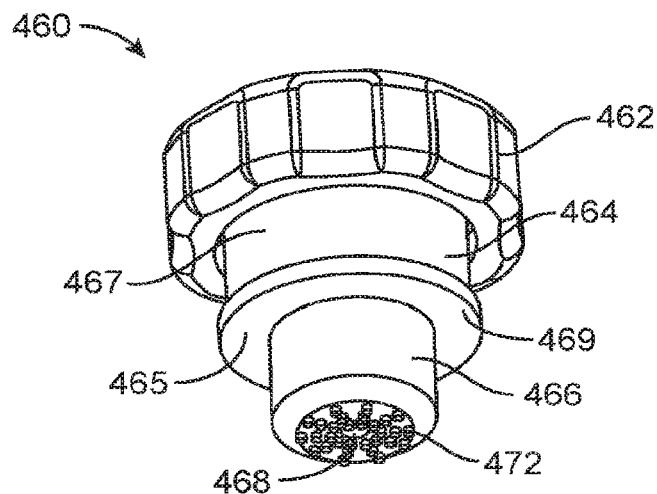
FIGS. 30A-30C illustrate yet another exemplary embodiment of an electrode assembly having a single, cylindrical tubular member on a bottom surface of a lower portion thereof and received within a buckle assembly to allow rotation when the buckle is attached to a headband.
Figure 30B:
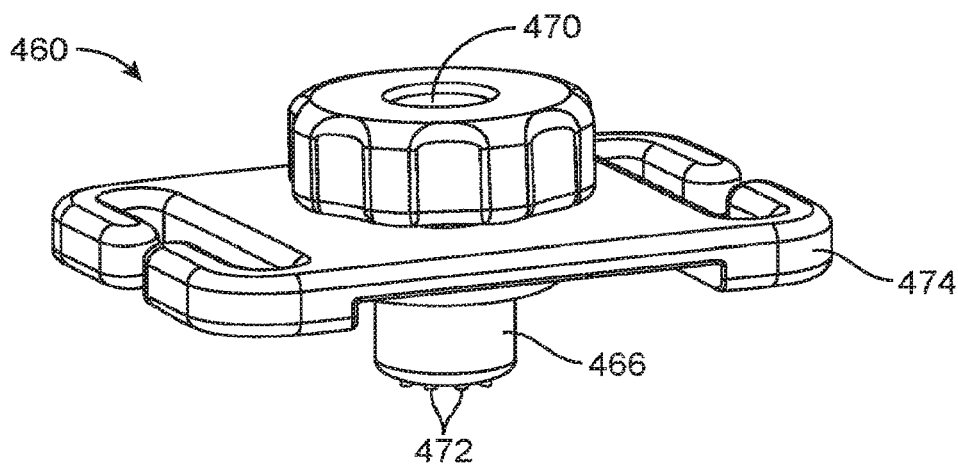
Figure 30C:
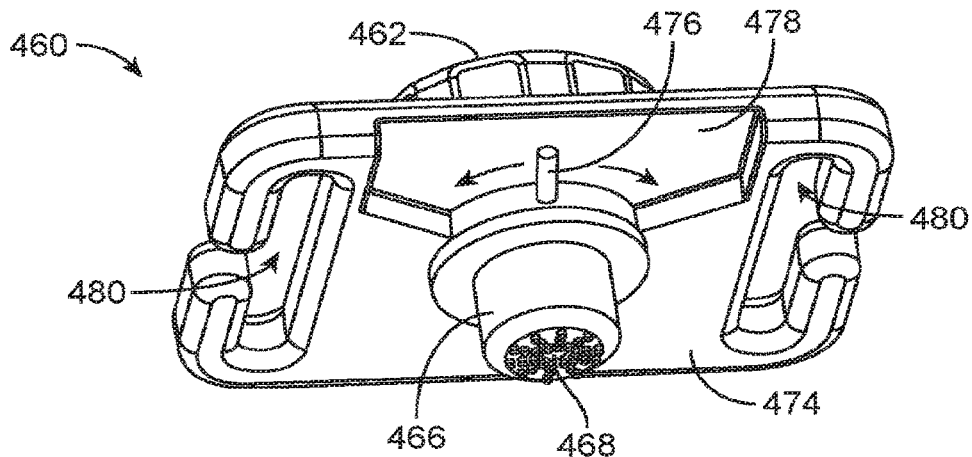

In yet another embodiment, an electrode assembly 460 constructed in accordance with the principles of the present invention comprises an upper portion or cap 462 secured to a lower portion or base 464, as illustrated in FIGS. 30A-30C. A single tubular member 466 projects downwardly from a bottom surface 465 of the lower portion or base 464. A vertical passage or port 468 extends from an upper or introductory port 470 through the upper and lower portions in order to allow introduction of an electrically conductive gel or other fluid. A lower surface of the single tubular member 466 comprises a number of surface features 472, generally as described elsewhere herein, in order to allow surface treatment or abrasion of the tissue before, during, or after introduction of the electrically conductive gel or other fluid through the vertical passage 468.

The electrode assembly 460 can be placed in a plate or buckle 474, typically through an opening, so that a channel 467 formed between the lower surface of the upper portion or cap 462 and a flange 469 on the lower portion or base 464 receives the wall of the plate 474 to allow rotation of the electrode assembly relative to the plate. An electrically conductive terminal 476 passes through a wall of the lower portion or base 464 so that it is in electrical contact with the electrically conductive gel or other fluid which passes through the vertical passage 468 in order to form an electrically conductive path with the tissue contacted by the lower surface of the single tubular member 466. The electrically conductive terminal 476 is free to move within a cut out region 478 on the lower surface of the buckle or plate 474 as indicated by the arrows on either side of the terminal. The buckle 474 includes side loops or cut outs 480 which permit the buckle to be attached to a strap in order to form a headband by joining the buckle to other similar structures.

Figure 31A:
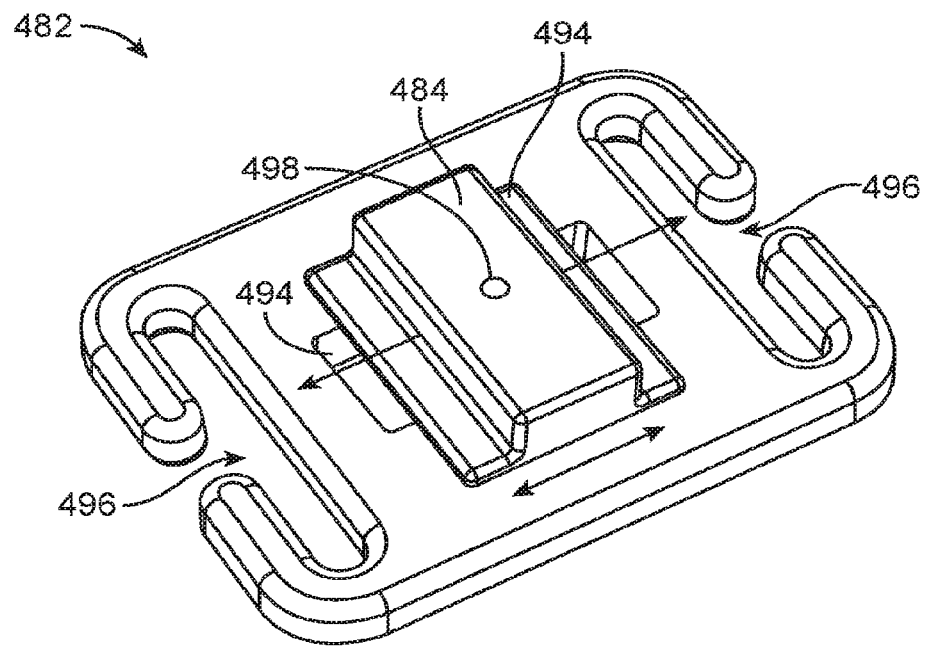
FIGS. 31A and 31B illustrates a still further exemplary embodiment of an electrode assembly constructed in accordance with the principles of the present invention where the electrode assembly is configured to axially translate within a slot of a buckle assembly.
Figure 31B:
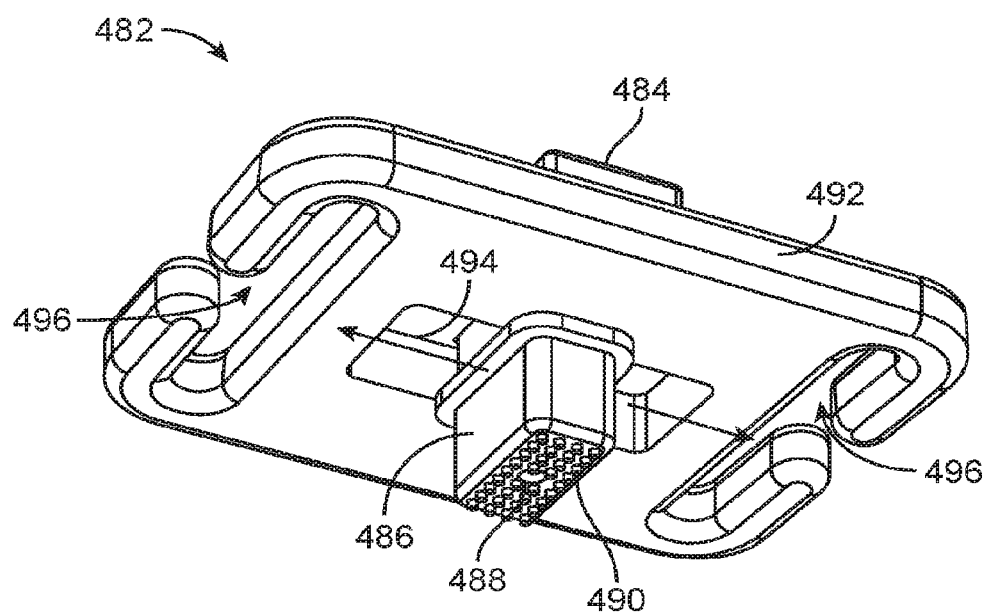

Referring now to FIGS. 31A and 31B, a still further electrode assembly 482 constructed in accordance with the principles of the present invention comprises an upper portion 484 and a lower portion 486. The electrode assembly 482 is received within a buckle or plate structure 492 so that it is free to slide within a slot 494 in the direction of the arrow shown in FIG. 31A. The electrode assembly 482 has a port 498 for receiving an electrically conductive gel or other fluid and distributing that fluid through a lower port 488 which is located in an array of surface features 490 on a lower surface of the lower portion 486. In this way, after the electrode assembly 482 is engaged against a patient's skin, typically as part of the headband, the electrode can be translated back and forth relative to the buckle 492 and headband in order to treat the skin surface and enhance electrical conductivity, as described in greater detail elsewhere herein. The buckle or plate 492 includes slots 496 on either side in order to facilitate attachment to the headband assembly.

The following numbered paragraphs further described the present invention:

31. A method for placing a plurality of electrodes on a patient's scalp, said method comprising:
    placing a headband around the patient's scalp, said headband carrying a plurality of electrode assemblies;
    engaging distal tip(s) of one or more tubular members extending from at least some of the electrode assemblies against scalp tissue;
    extruding a conductive fluid or gel from a reservoir disposed in at least some of the electrode assemblies through the tubular members of those electrode assemblies to form an electrically conductive path to the patient's scalp tissue; and
    connecting the plurality of electrode assemblies to a controller and/or output device configured to receive low power biological current from the electrode assemblies.
32. A method as in claim 31, wherein the distal tips of at least some of the tubular members are positioned through hair on the patient's scalp.
33. A method as in claim 31, further comprising moving at least some of the plurality of electrode assemblies to abrade scalp tissue adjacent the distal tip(s) of said one or more tubular members in order to lower contact resistance between the electrode assembly and the scalp tissue.
34. A method as in claim 33, the distal tips of at least some of the tubular members define a skin preparation surface.
35. A method as in claim 31, wherein the conductive fluid or gel is extruded from the reservoir through lumens in the tubular members and out of the distal opening(s) on distal tips of the tubular member(s) onto the scalp tissue.
36. A method as in claim 35, wherein the conductive fluid or gel is extruded out of groove(s) on the distal tips of the tubular member(s).
37. A method as in claim 31, wherein extruding the conductive fluid or gel from the reservoir comprises manually applying external pressure to a sealed dispensing container which holds the conductive fluid or gel, wherein the sealed dispensing container is incorporated into the electrode assembly.
38. A method as in claim 37, wherein applying external pressure to the sealed dispensing container comprises pressing a plunger to engage a rupturable sealed dispensing container that carries the conductive fluid or gel.
39. A method as in claim 37, wherein applying external pressure to the sealed dispensing container comprises manually squeezing a tube, manually depressing a syringe plunger, and rolling a squeeze tube
40. A method as in claim 31, wherein the electrically conductive path to the patient's scalp tissue is formed solely by the conductive fluid or gel.
41. A method as in claim 31, wherein the electrically conductive path to the patient's scalp tissue is formed at least partly by the electrically conductive structure on the tubular members.
42. A patient monitoring system, comprising:
    one or more electrodes configured for contacting a skin surface;
    a backing which is securable to a patient body and is further configured to maintain the one or more electrodes against the skin surface;
    at least one motion detection apparatus attached to the backing; and
    a controller for receiving electrical data from the one or more electrodes and motion data related to the at least one motion detection apparatus, wherein the controller is programmed to process the electrical data and motion data.
43. The system of claim 42 wherein the one or more electrodes each comprise an electrode body which is at least partially electrically conductive, one or more tubular members extending from the electrode body, each of the one or more tubular members defining a lumen therethrough and a distal opening.
44. The system of claim 43 further comprising a reservoir having a compressible structure and containing a conductive fluid or gel which is in fluid communication with the one or more tubular members.
45. The system of claim 42 wherein the backing is configured as a headband for placement upon a patient's head.
46. The system of claim 42 wherein the at least one motion detection apparatus comprises one or more fiducial markers.
47. The system of claim 46 further comprising an imaging apparatus configured to image the one or more fiducial markers.
49. The system of claim 47 wherein the imaging apparatus comprises a camera.

50. The system of claim 46 wherein the imaging apparatus is in communication with the controller.

51. The system of claim 42 wherein the at least one motion detection apparatus comprises one or more accelerometers.

The applications of the devices and methods discussed above are not limited to electrical sensing upon the patient's head but may include any number of further treatment applications. Moreover, such devices and methods may be applied to other treatment sites upon the body. Modification of the above-described assemblies and methods for carrying out the invention, combinations between different variations as practicable, and variations of aspects of the invention that are obvious to those of skill in the art are intended to be within the scope of the claims.

What is claimed is:

1. An electrode assembly comprising:
an electrode body comprising a reservoir, a horizontal passageway, and one or more members extending from the electrode body, the reservoir comprising a conductive fluid or gel and the one or more members comprising a vertical lumen directly connected to the horizontal passageway,
wherein the vertical lumen and the horizonal passageway are configured to deliver the conductive fluid or gel from the reservoir to the vertical lumen via the horizontal passageway.

2. The electrode assembly of claim 1, wherein the one or more members comprise a tubular member having a length and a width.

3. The electrode assembly of claim 2, wherein the length of the tubular member is at least two times the width of the tubular member.

4. The electrode assembly of claim 3, wherein the length of the tubular member is at least three times the width of the tubular member.

5. The electrode assembly of claim 2, wherein the length of the tubular member ranges from about 1 cm to about 2 cm.

6. The electrode assembly of claim 1, wherein the one or more members comprise one or more prongs.

7. The electrode assembly of claim 6, wherein the one or more prongs comprise a rigid material.

8. The electrode assembly of claim 7, wherein the rigid material comprises a metal or a conductive polymer.

9. The electrode assembly of claim 6, wherein the one or more prongs have a crescent shape.

10. The electrode assembly of claim 1, further comprising a channel or slot extending along a tissue-contacting surface of the one or more members.

11. The electrode assembly of claim 10, wherein the tissue-contacting surface comprises a skin preparation surface.

12. The electrode assembly of claim 11, wherein the skin preparation surface comprises an abrasive material.

13. The electrode assembly of claim 12, wherein the abrasive material comprises abrasive particles.

14. The electrode assembly of claim 11, wherein the skin preparation surface comprises a plurality of skin-roughening features.

15. The electrode assembly of claim 14, wherein the plurality of skin-roughening features comprises ridges, bumps, grooves, or a combination thereof.

16. The electrode assembly of claim 10, wherein the channel or slot is directly connected to the vertical lumen.

17. The electrode assembly of claim 1, wherein the reservoir comprises a sealed dispensing container.

18. The electrode assembly of claim 1, further comprising an electrically conductive terminal mounted on the electrode body and exposed to an electrically conductive path formed by the conductive fluid or gel, wherein the electrically conductive terminal is configured to be attached to external wiring.

19. An electrode carrier system comprising:
an elongated backing configured as a headband for placement upon a head of a patient;
a plurality of electrode assemblies as in claim 1 distributed over a length of the elongated backing; and
at least one electrically conductive wire connected to each electrode assembly to deliver EEG signals from the electrode assemblies to one or more of a controller and an output device.

20. The electrode carrier system of claim 19, further comprising one or more of the controller and the output device, which are configured to receive the EEG signals from the electrode assemblies.

21. The electrode carrier system of claim 19, wherein the controller is further configured to record the EEG signals from the electrode assemblies.

22. The electrode carrier system of claim 19, wherein the headband comprises one or more fiducial markers.

23. A method for measuring EEG signals comprising:
placing a headband around a head of a patient, the headband carrying a plurality of electrode assemblies as in claim 1;
delivering the conductive fluid or gel from the reservoir to the vertical lumen via the horizontal passageway to form an electrically conductive path to a skin surface of the patient's head; and
connecting the plurality of electrode assemblies to one or more of a controller and an output device configured to receive EEG signals from the electrode assemblies.

24. The method of claim 23, wherein the one or more members comprises a distal tip configured to be positioned through hair on the patient's head.

25. The method of claim 24, wherein the distal tip comprises a skin preparation surface.

26. The method of claim 25, wherein the skin preparation surface comprises an abrasive material.

27. The method of claim 26, wherein the abrasive material comprises abrasive particles.

28. The method of claim 25, further comprising rotating the plurality of electrode assemblies to abrade the skin surface in order to lower contact resistance between the electrode assembly and the skin surface.

29. The method of claim 23, wherein the reservoir comprises a sealed dispensing container and delivering the conductive fluid or gel comprises manually applying external pressure to the sealed dispensing container.

30. The method of claim 29, wherein applying external pressure comprises pressing a plunger against the sealed dispensing container.

* * * * *